(12) United States Patent
Knodel et al.

(10) Patent No.: US 6,425,900 B1
(45) Date of Patent: Jul. 30, 2002

(54) METHOD FOR ATTACHING HERNIA MESH

(75) Inventors: Bryan D. Knodel, Flagstaff, AZ (US); Bennie Thompson, Cincinnati; Michael R. Ludzack, Maineveille, both of OH (US)

(73) Assignee: Ethicon Endo-Surgery, Cincinnati, OH (US)

( * ) Notice: Subject to any disclaimer, the term of this patent is extended or adjusted under 35 U.S.C. 154(b) by 72 days.

(21) Appl. No.: 09/692,636

(22) Filed: Oct. 19, 2000

(51) Int. Cl.7 .............................................. A61B 17/10
(52) U.S. Cl. ...................... 606/139; 606/143; 606/158; 606/157; 606/151
(58) Field of Search ................................ 606/220, 232, 606/72, 139, 144, 75, 78, 145, 151, 219, 1, 158, 157, 143; 604/59; 24/711.1

(56) References Cited

U.S. PATENT DOCUMENTS

| | | | |
|---|---|---|---|
| 3,740,994 A | 6/1973 | DeCarlo, Jr. ................. 72/407 |
| 4,325,376 A | 4/1982 | Klieman et al. ............ 128/325 |
| 4,478,220 A | 10/1984 | Di Giovanni et al. ...... 128/326 |
| 4,527,724 A | 7/1985 | Chow et al. .................... 227/8 |
| 4,665,906 A | 5/1987 | Jervis .......................... 128/92 |
| 4,925,445 A | 5/1990 | Sakamoto et al. ............ 604/95 |
| 5,171,249 A | 12/1992 | Stefanchik et al. ......... 606/142 |
| 5,203,864 A | 4/1993 | Phillips ....................... 606/151 |
| 5,217,486 A | 6/1993 | Rice et al. ................... 606/232 |
| 5,290,297 A | 3/1994 | Phillips ....................... 606/144 |
| 5,470,010 A | 11/1995 | Rothfuss et al. ........... 227/177 |
| 5,562,704 A * | 10/1996 | Tamminmaki et al. ...... 606/151 |
| 5,571,104 A * | 11/1996 | Li ............................... 606/232 |
| 5,582,616 A | 12/1996 | Bolduc et al. .............. 606/143 |
| 5,601,573 A | 2/1997 | Fogelberg et al. .......... 606/143 |
| 5,662,654 A * | 9/1997 | Thompson ........... 128/DIG. 23 |
| 5,673,842 A | 10/1997 | Bittner et al. ............. 227/175.4 |
| 5,810,882 A | 9/1998 | Bolduc et al. .............. 606/213 |
| 5,830,221 A | 11/1998 | Stein et al. .................. 606/151 |
| 5,833,700 A | 11/1998 | Fogelberg et al. .......... 606/158 |
| 5,878,938 A | 3/1999 | Bittner et al. ............. 227/175.4 |
| 5,921,997 A | 7/1999 | Fogelberg et al. .......... 606/158 |
| 5,984,927 A * | 11/1999 | Wenstrom et al. .......... 606/213 |
| 6,007,566 A * | 12/1999 | Wenstrom, Jr. ............. 606/232 |
| 6,113,611 A | 9/2000 | Allen et al. .................. 606/151 |
| 6,290,702 B1 * | 9/2001 | Fucci et al. ................. 411/456 |
| 6,322,563 B1 * | 11/2001 | Cummings et al. ......... 606/104 |
| 6,325,805 B1 * | 12/2001 | Ogilvie et al. ................ 606/72 |

FOREIGN PATENT DOCUMENTS

| | | | |
|---|---|---|---|
| EP | 0392750 B1 | 1/1995 | ......... A61B/17/068 |
| WO | WO98/11814 | 3/1998 | ......... A61B/17/068 |

* cited by examiner

*Primary Examiner*—A. Vanatta
*Assistant Examiner*—Robert H. Muromoto, Jr.
(74) *Attorney, Agent, or Firm*—Dean L. Garner

(57) ABSTRACT

A method for delivering a plurality of individual surgical fasteners includes the steps of providing a surgical fastener delivery device. The delivery device has a drive mechanism having a distal and a proximal end, and a first and a second opposing member. The members are moveable proximally and distally with respect to the delivery device, and individually with respect to each other. The delivery device further includes a plurality of surgical fasteners located between the first and the second members. Next, the surgical fastener delivery device penetrates tissue by moving the drive mechanism distally. A distal end of one of the fasteners is partially deployed by moving the first member proximally. Finally, the distal end of the fastener is fully deployed by moving the second member proximally.

14 Claims, 20 Drawing Sheets

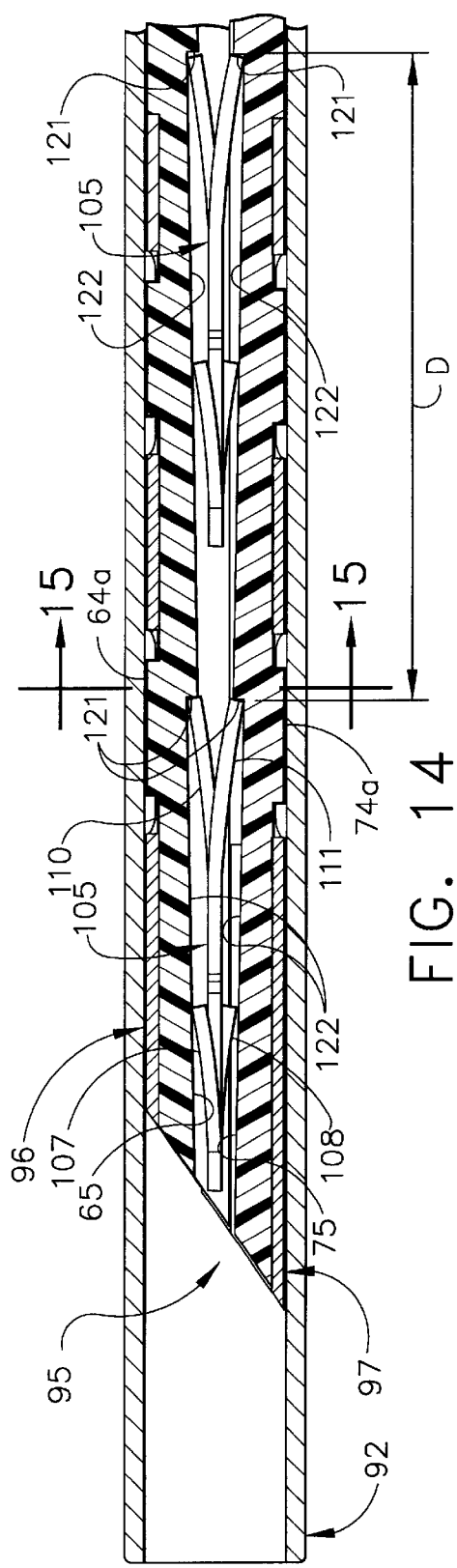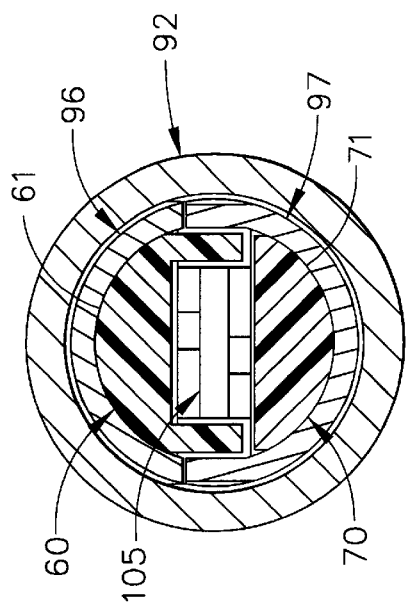

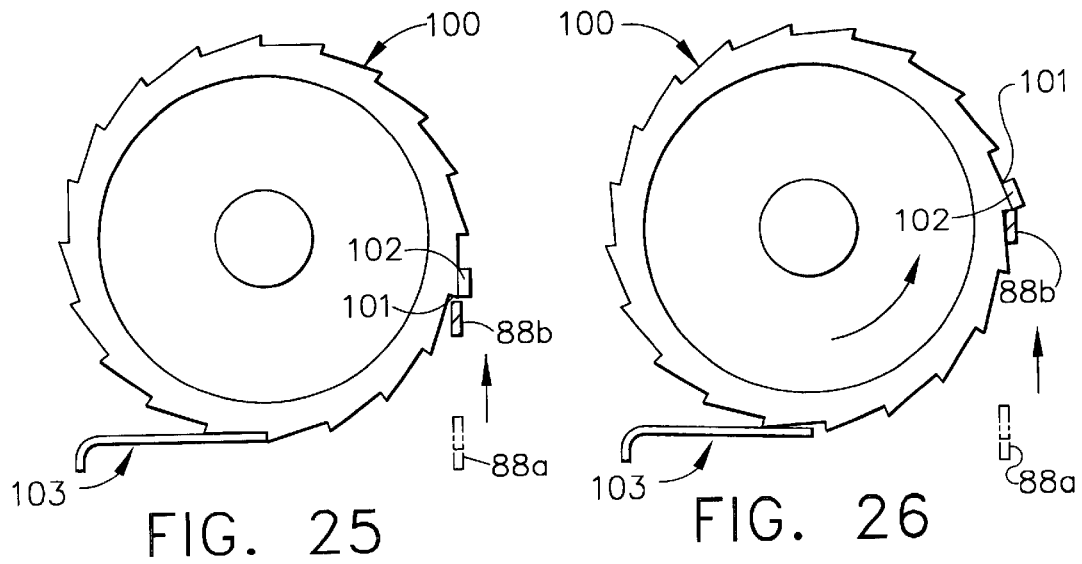
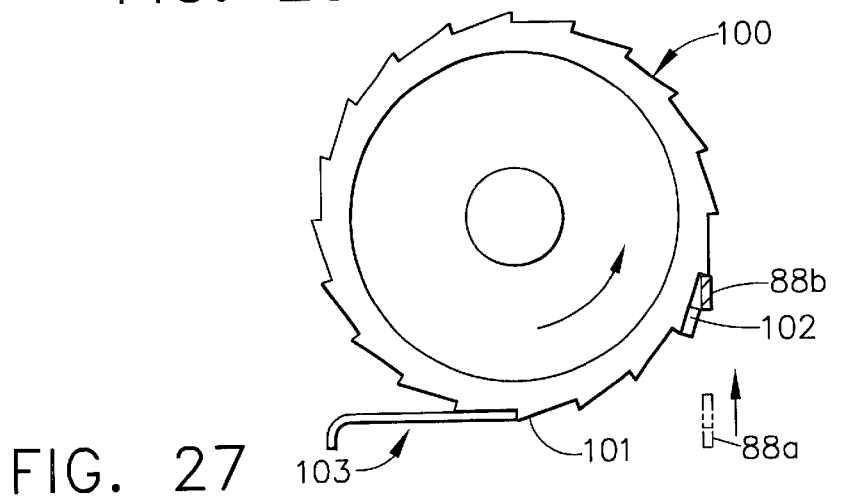
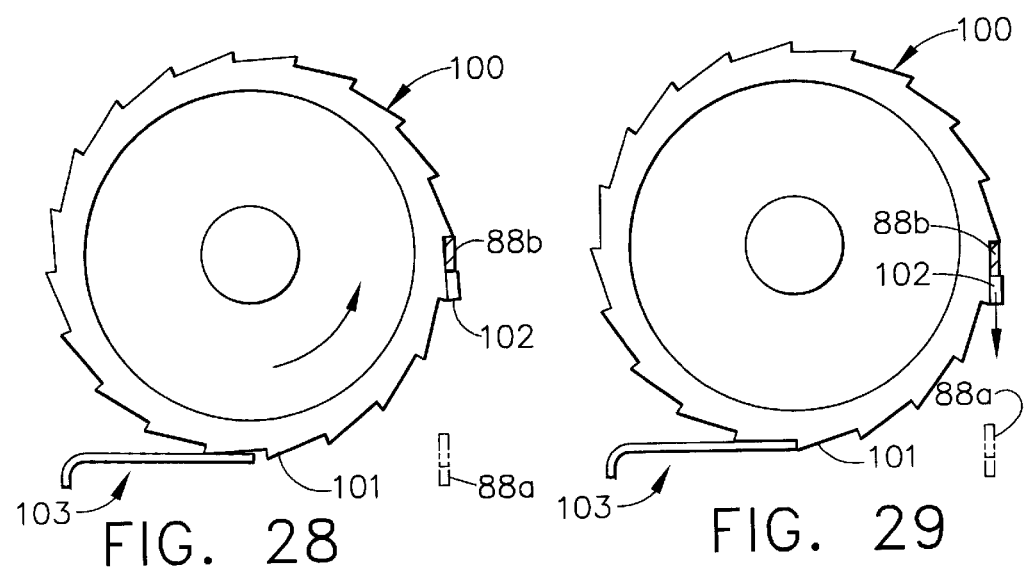

METHOD FOR ATTACHING HERNIA MESH

This application is related to the following copending patent applications: application Ser. No. 09/692,633, Ser No. 09/692,635, and application Ser. No. 09/692,627, which are hereby incorporated herein by reference.

FIELD OF THE INVENTION

The present invention relates, in general, to the repair of defects in tissue and includes a novel surgical method for placing a surgical element into tissue with a surgical instrument. More particularly, to the method of use of the surgical fastening instrument and surgical fastener in combination with a prosthetic for the repair of an inguinal hernia.

BACKGROUND OF THE INVENTION

It is established practice in the surgical field to repair defects in tissue, for instance, an inguinal hernia, through the use of PROLENE™ mesh (manufactured and sold by Ethicon, Inc., Somerville, N.J.). Generally the mesh is cut to a desired size for placement over the inguinal hernia. Once the sized mesh has been placed over the defect, the mesh is attached to the surrounding inguinal tissue using several known attachment means.

Once the mesh is in place, it is important that the mesh serve as a barrier over the defect in order to restrict the lower viscera in the patient's abdomen from protruding through the defect. Accordingly, it is essential that the attachment means used to secure the mesh to the inguinal tissue have an initial strength of several pounds of force in both the tensile and shear directions. Moreover, it is important that the mesh remain in place for several days so that natural adhesions can form to ensure that the mesh is sufficiently anchored to the tissue.

One common way of attaching the mesh to tissue is through the use of suture and needle. As would be expected, the suturing technique for this procedure requires a great deal of skill and is normally conducted by very experienced surgeons, especially for minimally invasive or laparoscopic procedures. Since the learning curve for laparoscopic suturing is extremely steep, many surgeons are slow to adopt this technique.

In response to the challenges associated with suturing, other fastening techniques have evolved such as the use of a surgical element or surgical fastener. Accordingly, it is now common practice to use a surgical stapler such as the ENDOSCOPIC MULTI-FIRE STAPLER™, (manufactured and sold by Ethicon Endo-Surgery, Inc., Cincinnati, Ohio). U.S. Pat. No. 5,470,010 by Robert Rothfuss et al. and in U.S. Pat. No. 5,582,616, also by Robert Rothfuss et al. disclose disposable endoscopic staplers of this type. These staplers are used to place a number of staples at various locations of the placed mesh in order to properly secure the mesh to the tissue. Although the endoscopic stapler is efficient and easy to use for a surgeon, the shaft diameters are on the order of 10 mm in diameter. Some surgeons believe that a smaller diameter instrument is better for endoscopic procedures and have begun to use smaller 5 mm devices that offer a reduced access incision in the abdomen and slightly better visibility.

In addition to using surgical staplers to secure mesh to inguinal tissue to repair a hernia, other types of fasteners have been developed. One of these fasteners is a helical fastener such as disclosed in U.S. Pat. No. 5,582,616 by Lee Bolduc et al., U.S. Pat. No. 5,810,882 by Lee Bolduc et al., and in U.S. Pat. No. 5,830,221 by Jeffrey Stein et al. A plurality of helical wire fasteners are stored serially within the 5 mm shaft, and are corkscrewed or rotated into tissue to attach the mesh. However, although these types of fasteners are also easy to use and decrease the procedure time, the long length and sharp end of the fastener can be an issue in thin tissue.

Other surgical fasteners and surgical application instruments have been tried for example plastic or stainless steel dart fastener having a pointed distal end with retaining barbs, and a large disk at the proximal end. A single shot plunger type applicator is used, and for multiple firings, a rotary magazine is employed. This type of fastener and surgical fastening instrument can be found in U.S. Pat. No. 5,203,864 (Edward Phillips). To apply, the surgeon drives the pointed end into the mesh patch and into tissue. Whereas the dart fasteners appear to be effective in fastening mesh to tissue, they have not gained acceptance within the surgical community possibly due to their single shot capabilities and the large size of the rotary magazine.

Another plastic fastener is the "H" shaped clothing tag fastener. This a fastener is best known for attaching tags to clothing. The fasteners are placed into tissue with a single shot instrument. The instrument and fastener are described in U.S. Pat. No. 5,290,297 by Edward Phillips. These fasteners and instruments are also relatively unknown by surgeons, possibly due to their single shot capabilities.

It is important to note that, presently, the known devices or attachment means for repairing tissue defects are endoscopic staplers, helical fastening instruments, fasteners, or simple needle and suture. Presently, there are no known surgical fastening methods that pierce tissue with the surgical instrument, and deliver a surgical element or fastener into tissue. Additionally, there are no known hernia fastening devices that place a blunt fastener into tissue. Also, it would be desirable for the surgical element or fastener to be used as a marker that can appear on MRI examinations, X-rays, or ultrasound. Thus, there are no known surgical fastening instruments or fastening methods that can meet all of the needs outlined above.

SUMMARY OF THE INVENTION

A method for delivering a plurality of individual surgical fasteners includes the steps of providing a surgical fastener delivery device. The delivery device has a drive mechanism having a distal and a proximal end, and a first and a second opposing member. The members are moveable proximally and distally with respect to the delivery device, and individually with respect to each other. The delivery device further includes a plurality of surgical fasteners located between the first and the second members. Next, the surgical fastener delivery device penetrates tissue by moving the drive mechanism distally. A distal end of one of the fasteners is partially deployed by moving the first member proximally. Finally, the distal end of the fastener is fully deployed by moving the second member proximally.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 14 is a cross-sectional side view of a distal end of a shaft of the surgical instrument of the present invention showing the end effector normally retracted therein and a plurality of surgical fasteners of the preferred invention contained therein;

FIG. 15 is a cross-sectional view 10—10 of the shaft and the end effector of FIG. 9 and showing a passageway and a fastener of the preferred invention contained therein;

FIG. 25 is a fragmentary cross-section view of the lockout mechanism of the present invention showing the lockout wheel in an initial position and engaged with a wheel detent, wherein the lockout arm is moving upwardly from a start position (dashed lines) to a second position (cross section) adjacent to the lockout wheel;

FIG. 26 is a fragmentary cross-section view of FIG. 25 showing the upwardly moving lockout arm engaging with a first tooth of the lockout wheel, wherein the engagement has rotated the locking wheel one tooth counterclockwise and the locking arm is preparing to return to the initial position (dashed lines);

FIG. 27 is a fragmentary cross-section view of FIG. 26 showing the upwardly moving lockout arm engaging with a final tooth of the lockout wheel, wherein the repeated firing of the trigger has rotated the lockout wheel to the final tooth, and a locking tab is positioned just below the upwardly moving locking arm (cross section);

FIG. 28 is a fragmentary cross-section view of FIG. 27 showing the upwardly moving lockout arm further engaging with a final tooth of the lockout wheel, wherein the lockout wheel has rotated counterclockwise to position the locking tab below the lockout arm;

FIG. 29 is a fragmentary cross-section view of FIG. 28 showing the detent arm preventing further rotation of the locking wheel and the lockout arm attached to the trigger captured between a tooth and the locking arm of the locking wheel.

DETAILED DESCRIPTION OF THE INVENTION

The present invention pertains to a novel surgical method for the repair of tissue defects in a human patient. More particularly, the invention concerns a novel surgical method for using a surgical instrument and a surgical element or fastener to attach a prosthetic in the repair of an inguinal hernia.

By way of example, the present invention is illustrated and described in conjunction with a repair of an inguinal hernia. However, it should be understood that the present invention is applicable to various other surgical procedures that require the repair of defects in tissue.

The Surgical Instrument

Figure 1:
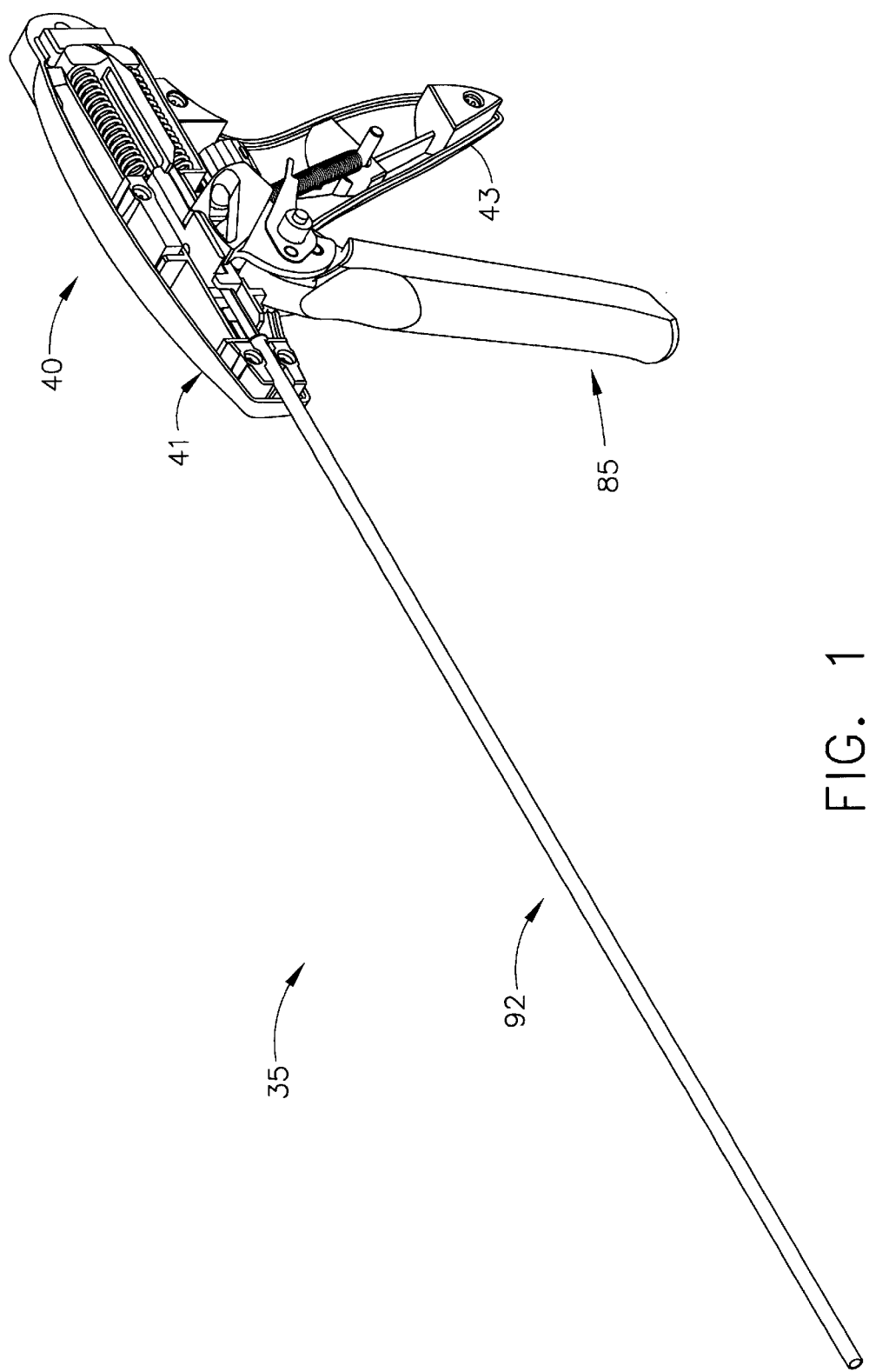
FIG. 1 is an isometric view of a surgical instrument wherein a left handle half is removed to show the elements within and a trigger is in an open position.
Figure 2:
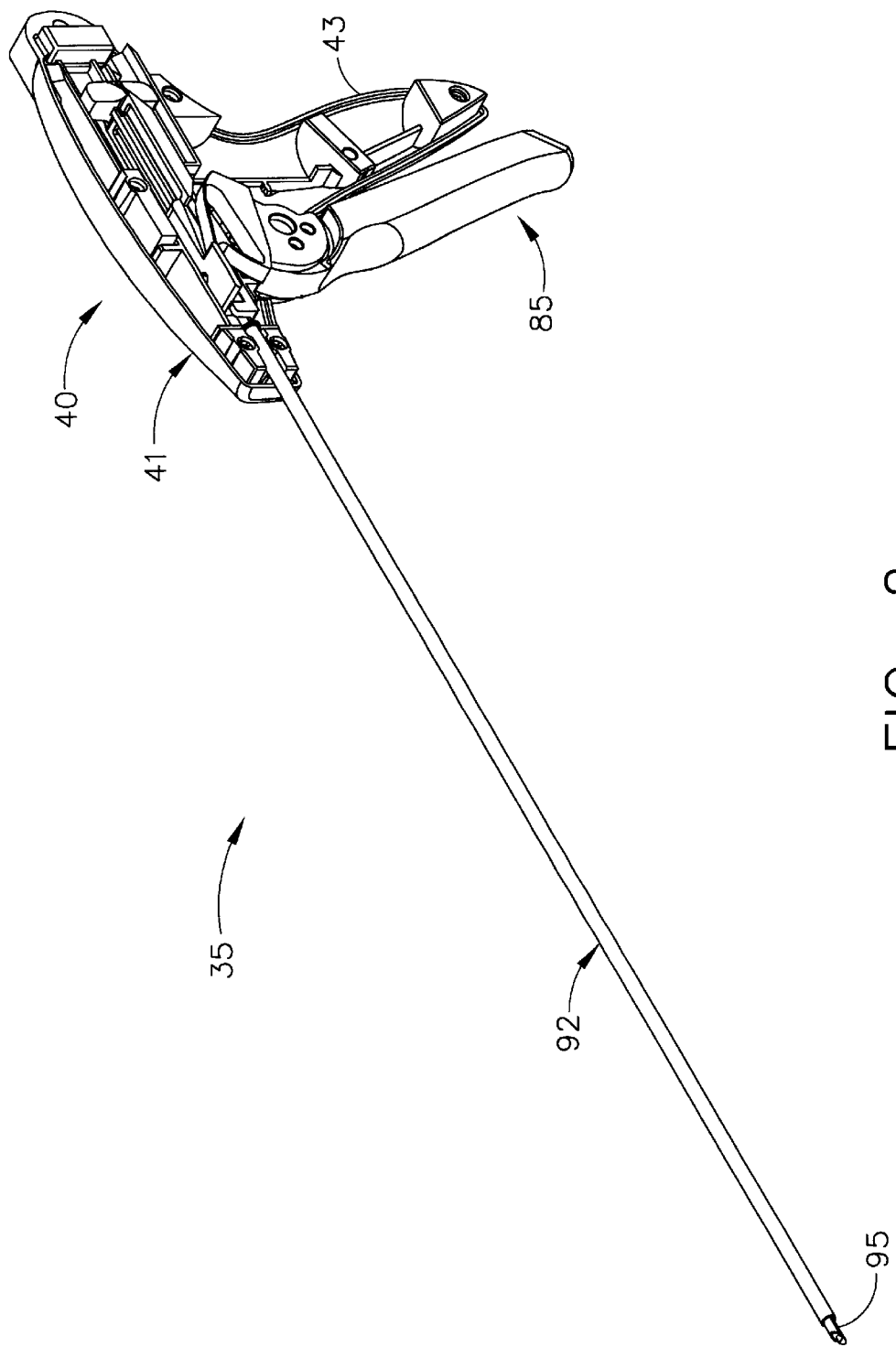
FIG. 2 is an isometric view of the surgical instrument of FIG. 1 wherein the trigger is moved from the open position of FIG. 1 to a closed position as shown, and an end effector is extended from the surgical instrument.

As best shown in FIGS. 1 and 2, the surgical instrument or delivery device includes a hand held surgical instrument 35 containing a plurality of surgical fasteners or surgical elements that are generally used for the attachment of a prosthetic to tissue, or as a tissue marker. The surgical fasteners 105 of the present invention are formed from a superelastic nickel titanium alloy, are stored within the surgical instrument in a compressed or collapsed state, and expand to an unconstrained state upon release from the surgical instrument. Actuation of the instrument simultaneously releases a fastener 105 of the present invention from a distal end of the instrument and indexes the plurality of fasteners 105 within the instrument.

Surgical instrument 35 of the present invention has a handle 40, an elongated shaft 92 extending distally from the handle 40, and a trigger 85 extending downwardly from the handle 40. Handle 40 has a right half 41 and a left half 42 that are generally mirror images of each other and, in FIGS. 1 and 2, the left half 42 is omitted. Elongated shaft 92 is fixedly attached to the handle 40, and is formed from a rigid hollow material such as stainless steel tubing. A grip 43 is fixedly attached to and extends downwardly from a proximal end of handle 40 and adjacent to the trigger 85. Trigger 85 pivotably mounts within handle 40 and is moveable from an open position as shown in FIG. 1 to a closed position adjacent to the grip 43 as shown in FIG. 2. Movement of the trigger 85 to the closed position extends an end effector 95 from a distal end of the shaft 92 (FIG. 2) for the placement and release of a fastener.

Figure 2B:
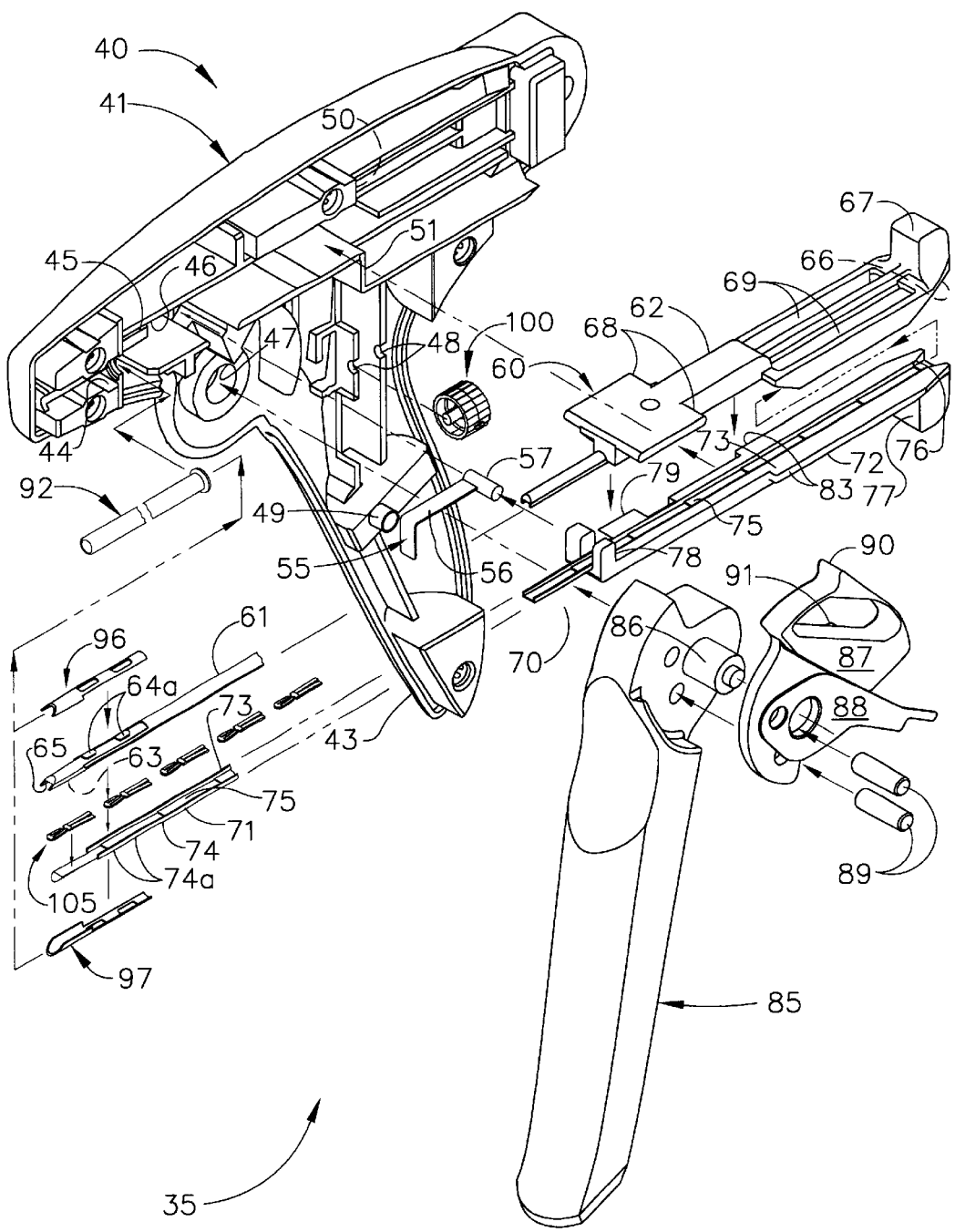
FIG. 2B is an exploded isometric view of some of the internal elements of the surgical instrument of FIG. 1, with some elements removed for clarity.

FIG. 2B is an isometric exploded view of the majority of the elements found within the surgical instrument 35. The exploded view is provided to familiarize the reader with the key elements contained therein, and the method of assembly used to form the surgical instrument 35. For clarity, a number of elements such as the left handle half 42 are removed. Some of the elements of FIG. 2B are complex in shape and the reader is advised to return to this figure for identification or comprehension of features referenced below. The elements of the surgical instrument 35 are contained within the right and left handle halves 41, 42 which can be formed from an engineering thermoplastic such as styrene, polycarbonate, or any one of a number of suitable materials. A shaft slot 44 is located at the distal end of the upper portion of the handle halves 41, 42 for the reception and retention of the shaft 92 therein.

A latch slot 45 is located proximally to and below the shaft slot 44 within the right handle half 41. Latch slot 45 is right-angled in shape and is provided for the reception of a latch 55 therein. Latch 55 has a rigid latch post 57 at a distal end and a right-angled beam 56 extending distally therefrom. Beam 56 is formed from a resilient spring material such as stainless steel. A distal end of beam 56 is captured and held within the latch slot 45 with a significant amount of the beam 56 cantilevering therefrom. The cantilever portion of the beam 56 enables the latch post 57 to move freely up and down as the beam 56 deflects. The significance of the latch 55 will be described later.

A first and a second slider 60, 70 are opposing members that extend generally proximally and distally throughout the shaft 92 and handle 40 of the surgical instrument 35 and form a drive mechanism for the fasteners 105. First and second sliders 60, 70 are moveable proximally and distally with respect to the surgical instrument 35 and individually with respect to each other, and are slidably retained within a pair of guide slots 46 located within each of the handle halves 41, 42. In FIG. 2B, the first and second sliders 60, 70 have a proximal and a distal end and are shown spaced apart prior to assembly to show a plurality of fasteners 105 that are stored therebetween. Fasteners 105 extend along the entire length of the first and second sliders 60, 70. First and second sliders 60, 70 have distal first and second feed members 61, 71 that slidably mount within the shaft 92, and a larger proximal first and second sequencing member 62, 72 that slidably mount within the handle halves 41, 42. First and second feed members 61, 71 are semi-circular in cross section and have a first and second outer surface 64, 74. A pair of first and second stab posts 64am, 74a extends outwardly from a distal end of each first and second outer surface 64, 74 respectively. A first and second contact surface 63, 73 completes the semi-circular cross section of the first and second feed members 61, 71 respectively. First and second contact surfaces 63, 73 opposably face each other along the entire length of the first and second sliders 60, 70 and have a first and second fastener channel 65, 75 extending therein. When assembled, first and second sliders 60, 70 make sliding contact along the entire length of first and second contact surfaces 63, 73 and first and second fastener channels 65, 75 form a hollow rectangular channel for the holding and feeding of fasteners 105 serially therethrough (FIG. 15).

The fastener channels 65, 75 of the first and second sliders 60, 70 are "U" shaped for the reception of the fasteners 105 therein and have a pair of opposed inner surfaces or channel floors for engaging with the fasteners 105. The inner surfaces have a plurality of projections or fastener drive features spaced thereon for engagement with the fasteners 105. As best shown in the enlarged FIG. 14, these projections or sawteeth 120, extend proximally to distally along the entire length of the floors of the first and second fastener channels 65, 75 and are equally spaced a longitudinal distance "D" apart. The distance "D" is between 8 inches and 0.005 inches. The spacing "D" of the present invention is 0.475 inches. The spacing "D" can space the fasteners apart from one another so that the fasteners do not engage or touch as they are fed within the surgical instrument 35. Each sawtooth 120 has a proximal incline 122 and a distal step 121 as shown. The role of the sawteeth 120 in the feeding of the fasteners 105 will be discussed in detail later.

At the distal end of the first and second fastener channels 65, 75 are a first and a second fastener guide 66, 76 respectively which are a tapered lead-in at the proximal end of fastener channels 65, 75 to assist in the loading of the fasteners 105 therein. These fastener guides 66, 76 are generally mirror images of each other. In FIG. 2B, the first fastener guide 66 is hidden.

The larger proximal portions of the first and second sliders 60, 70 are the first and second sequencing members 62, 72, which control the timing and sequencing of a fastener feeding mechanism that releases a fastener from the distal end of the instrument, and indexes or feeds the plurality of fasteners distally within the instrument. The first sequencing member 62 has a pair of guide ribs 68 extending laterally outwardly from either side and a first spring stop 67 extending upwardly at a proximal end. Guide ribs 68 mount within the guide slots 46 of the right and left handle halves 41, 42 and slidably secure the assembled sliders 60, 70 within the handle 40. A pair of "C" shaped guide channels 69 are located underneath and extend longitudinally along the proximal half of the first sequencing member 62. The second sequencing member 72 has second spring stop 77 located at a proximal end of second sequencing member 72 and a forked stop 78 extending upwardly at a distal end. A cam plate 79 extends outwardly from the far side of the second sequencing member 72 towards the right handle half 41. A pair of slider ribs 83 extends laterally outward along the proximal half of the second sequencing member 72. First and second sliders 60, 70 can be formed as a single piece from an engineering thermoplastic such as a liquid crystal polymer, a polycarbonate, nylon, a styrene or the like.

The first and second sliders 60, 70 are slidably interlocked together by inserting the pair of slider ribs 83 located on the second sequencing member 72 into the pair of guide channels 69 of the first sequencing member 62. First and second sliders 60, 70 are made sharp by the attachment of penetrating members or first and second stab plates 96, 97 thereon. First and second stab plates 96, 97 are then attached to the first and second sliders 60, 70 by placing first and second stab plates 96, 97 over first and second stab posts 64a, 74a and then placing the assembled stab plates 96, 97 and first and second sliders 60, 70 into the hollow shaft 92 to form a shaft sub-assembly. This method of stab plate retention is best shown in FIG. 14. Stab plates 96, 97 are used to pierce tissue during the placement of a fastener 105 into tissue and can be made from a rigid material such as stainless steel.

Next, the shaft sub-assembly is placed into an fastener feeding station (not shown) and the fastener 105 are fed one at a time into the first and second fastener guides 66, 76 and into the hollow channel formed from fastener channels 65, 75. The fastener 105 is inserted until the fastener 105 engages with the feeding mechanism, which will be described later. Once the fastener 105 is in place, the first and second sliders 60, 70 are reciprocated proximally and distally relative to a one another to feed or index the fastener 105 further into the shaft sub-assembly. This process is repeated for each new fastener 105 until the first and second sliders 60, 70 are fully loaded with a plurality of fasteners 105 in a serial fashion. The plurality of fasteners 105 are equally spaced along the entire length of the first and second sliders 50, 60. The shaft sub-assembly containing the fastener 105 is then placed into the right handle half 41. Shaft 92 is received in shaft slot 44 and the guide ribs 68 of the first slider 60 are slidably placed into the guide slot 46. Next, a lockout wheel 100 is placed into a wheel receptacle 48 located within the right handle half 41 at a position proximal to the pivot bore 47.

A trigger assembly is constructed by placing a trigger plate 87 and a lockout arm 88 over a pivot 86 that extends laterally on either side of trigger 85 and fixably attaching them to trigger 85 with a pair of pins 89. A drive arm 90 extends upwardly from the trigger plate 87 and a spring post 91 extends from the far side of the trigger plate 87 towards the right handle half 41. An end of a trigger spring 104 (FIG. 3) is then placed over spring post 91. The trigger assembly is then placed into the right handle half 41 by placing the far side pivot 86 (not shown) into a pivot bore 47. Trigger 85, trigger plate 87, and lockout arm 88 are shown as separate pieces but can alternately be constructed as a single piece from an engineering thermoplastic such as polycarbonate, styrene or the like.

Figure 3:
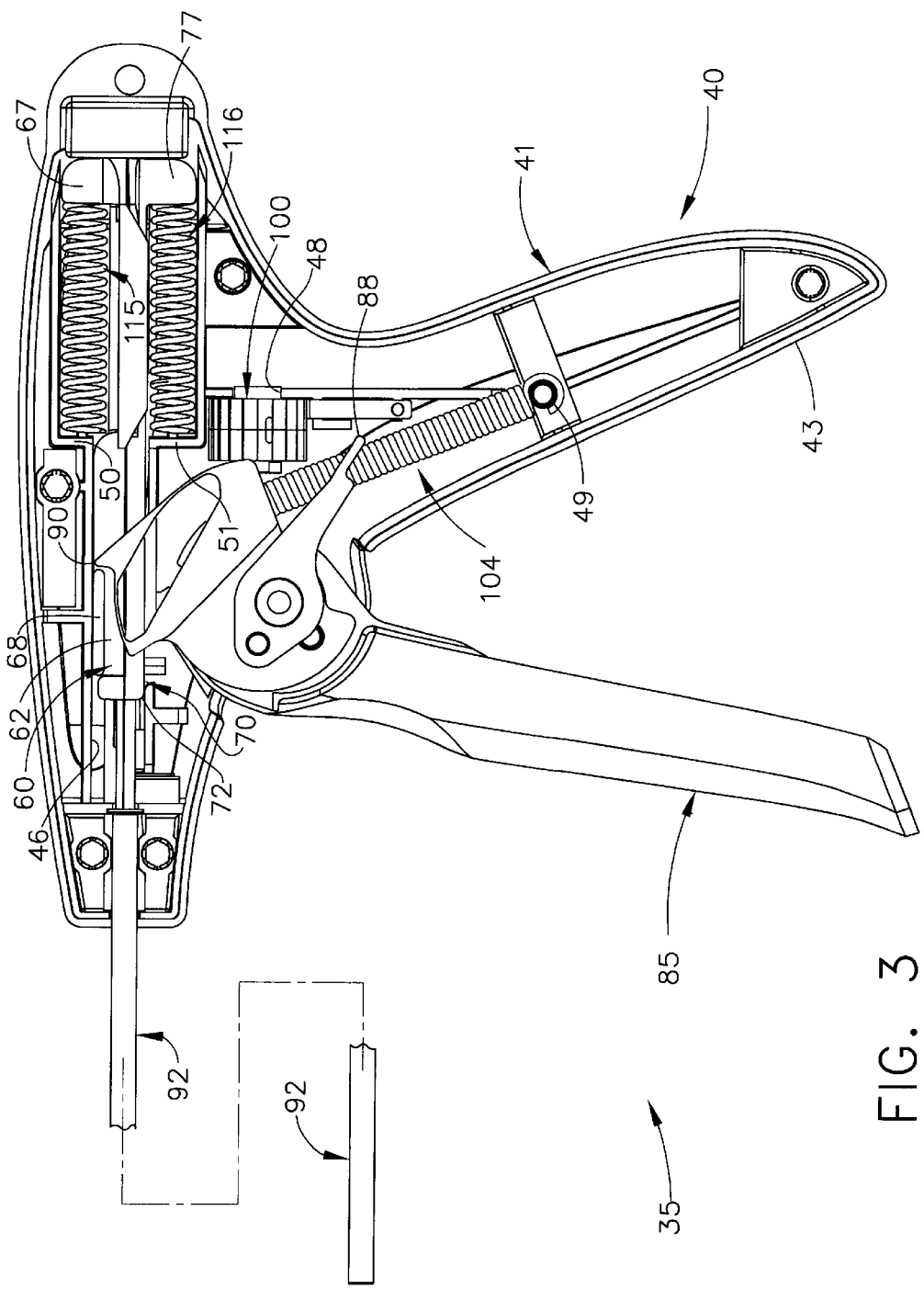
FIG. 3 is a side view, in cross section, of a first side of the surgical instrument of FIG. 1 with the left handle half removed, wherein all of the internal elements are shown assembled and the trigger is in an open position.

FIG. 3 shows the fully assembled elements of the handle 40. Prior to the view shown in FIG. 3, the free end of the trigger spring 104 has been stretched and attached to a spring pin 49 of the grip 43. The attachment of the free end of the trigger spring 104 tensions trigger spring 104, and biases the trigger 85 to the open position shown. Next, a first return spring 115 was compressed and placed into a first spring pocket formed between the first spring stop 67 of the first slider 60 and a first spring rib 50 of the handle halves 41, 42. A second return spring 116 was also compressed and placed into a second spring pocket formed between the second spring stop 77 of the second slider 70 and a second spring rib 51. Finally, the left handle half 42 was attached to the right handle half 41 to complete the assembly of the surgical instrument 35. The left handle half 42 has been removed for clarity.

The Actuator Mechanism

The instrument of FIGS. 3–8 shows the operation of the actuator or sequencing mechanism that controls the timing and movement of elements within the surgical instrument 35. The actuator mechanism engaged by the actuation of the trigger 85 and moves the drive mechanism or first and second sliders 60, 70 into at least three sequential positions. Actuation of the trigger 85 simultaneously moves the first and second sliders 60, 70 distally from a first proximal position to a second distal position, then returns the first slider 60 to the proximal position, and finally returns the second slider 70 to the proximal position. This sequence of motion advances the plurality of fasteners 105 distally, and deploys the distal end of the fastener into tissue in two steps. The actuator mechanism consists of the latch 55; the trigger assembly described above, the first and second return springs 115, 116, the first and second sliders 60, 70.

FIG. 3 shows a first or left side view of the surgical instrument of FIG. 1 with the right handle half 41 in place, the left handle half 42 removed for clarity, and the trigger 85 in the initial open position. The first and second sliders and second return springs 115, 116 are biasing the first and second sliders 60, 70 distally within the handles 41, 42. The trigger 85 of the trigger assembly is in the full open position with the drive arm 90 poised to operatively engage a proximal end of the guide rib 68 of the first sequencing member 62. First and second sliders 60, 70 are in the first proximal position.

Figure 4:
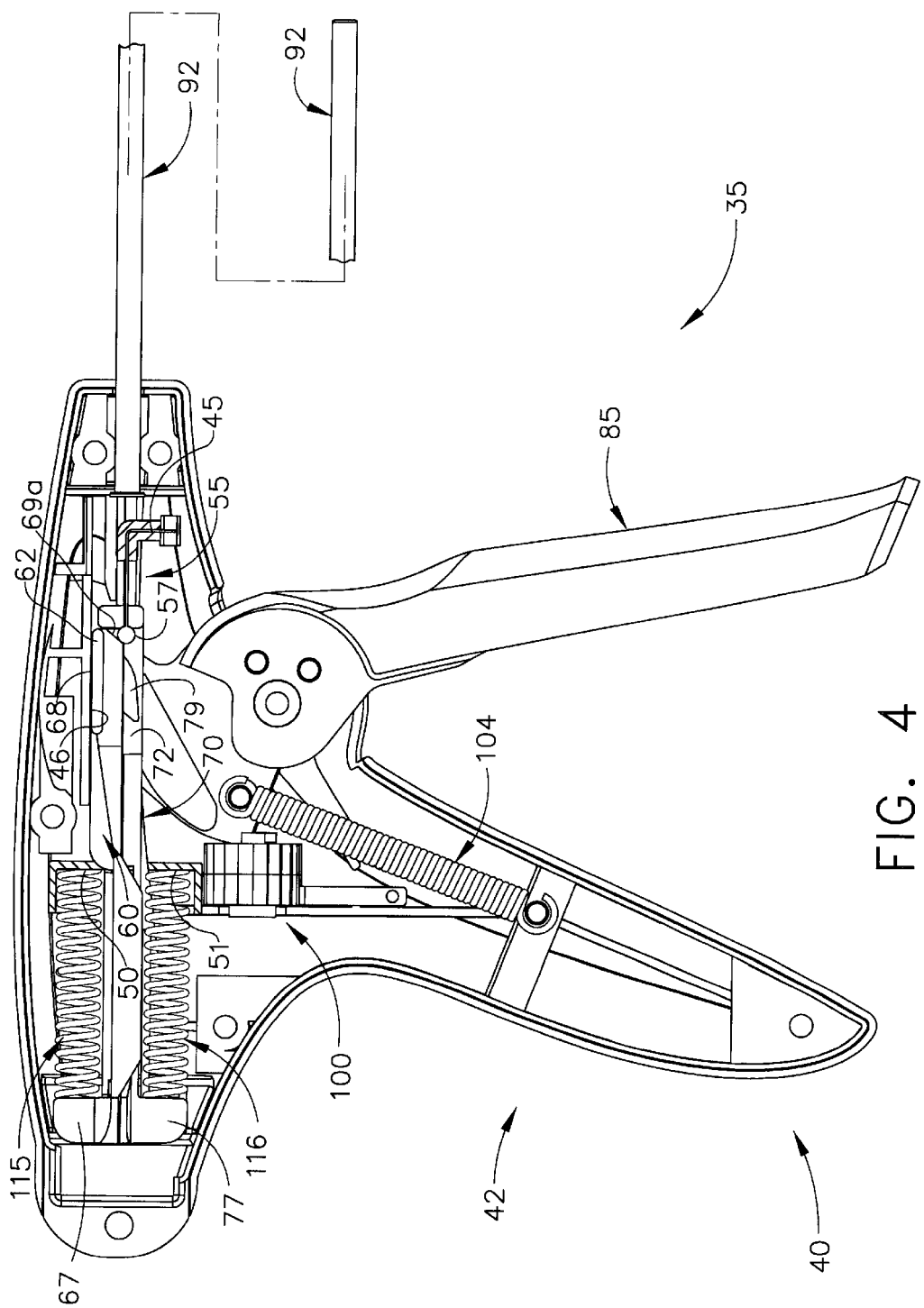
FIG. 4 is a side view of a second side of the surgical instrument of FIG. 3 with the left handle half in place and with the right handle half removed, showing all of the internal elements therein and the trigger in an open position.

FIG. 4 shows the second or right side view of the surgical instrument of FIG. 3 with the left handle half 42 in place and with the right handle half 41 removed. The latch 55 is visible in this view, and the latch post 57 of latch 55 is operatively engaged with a first ramp 69a located on the distal end of the first sequencing member 62. A portion of the first and second spring ribs 50, 51 and the latch slot 45 of the right handle half 41 are shown in cross-section for clarity.

Figure 5:
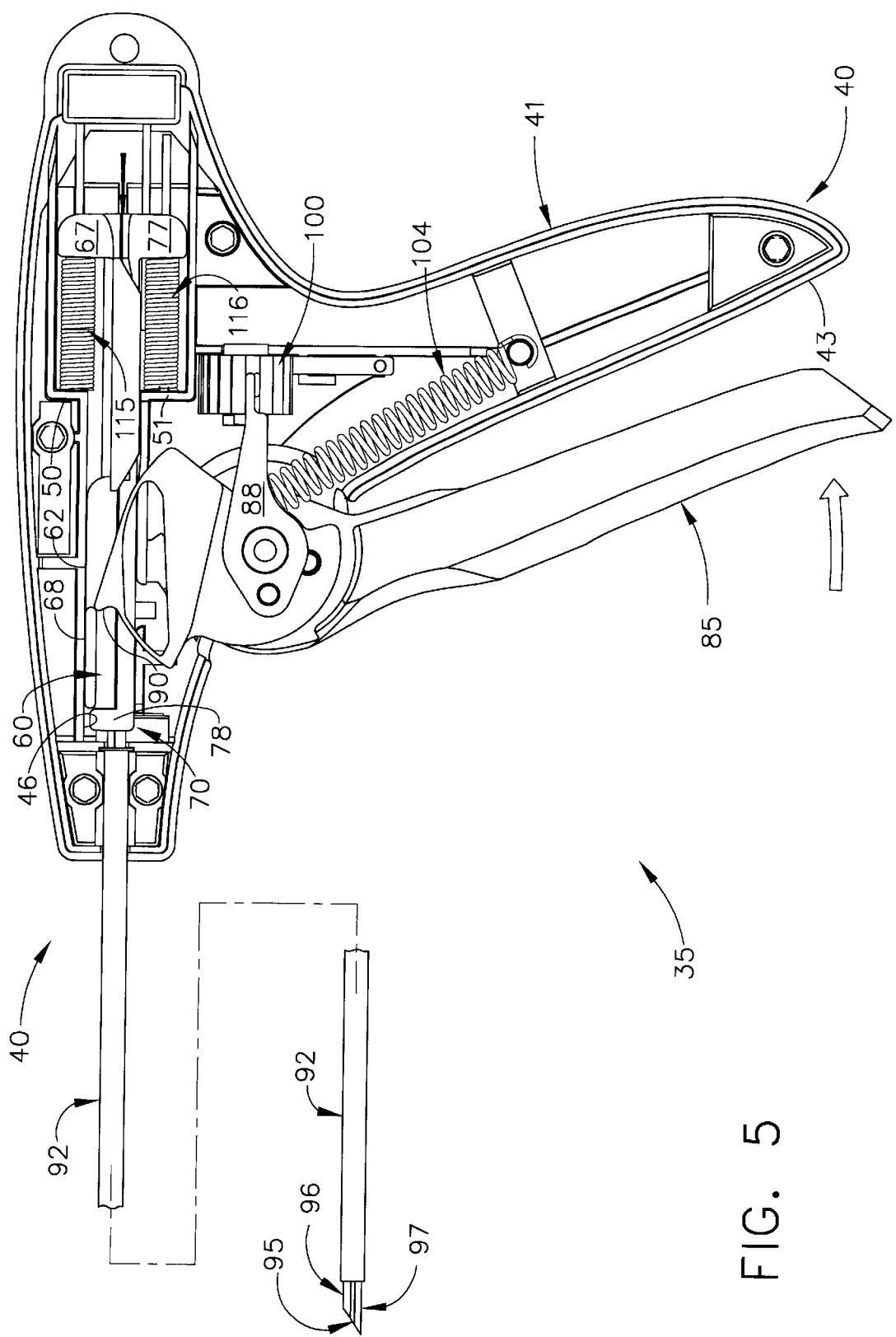
FIG. 5 is a side view of the first side of the surgical instrument of FIG. 3 wherein the trigger is moved to a partially closed position to extend the end effector from the surgical instrument.
Figure 6:
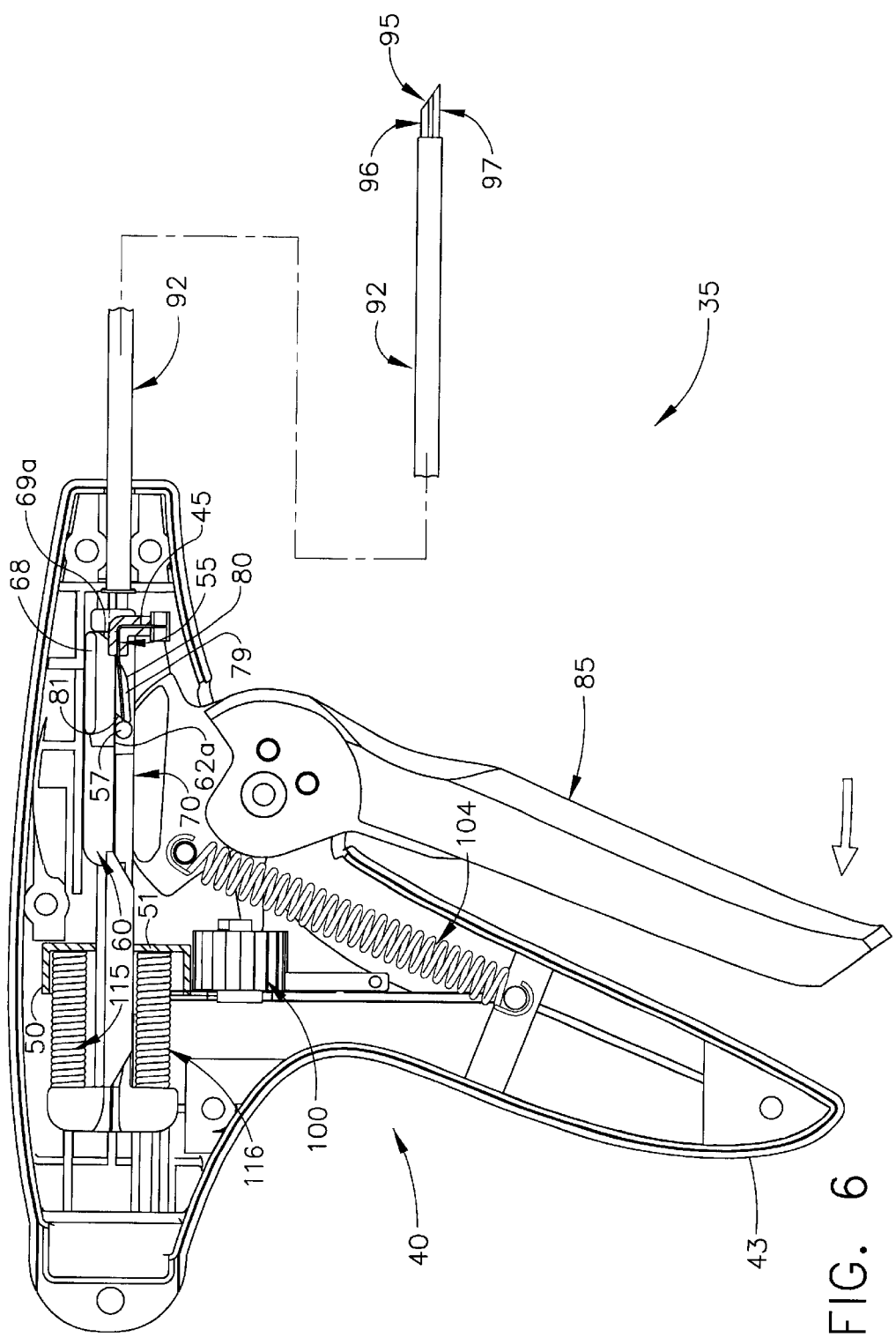
FIG. 6 is a side view of the second side of the surgical instrument of FIG. 5, wherein the trigger is moved to a partially closed position to extend the end effector from the surgical instrument.

FIGS. 5 and 6 show the left and right side views of the assembled surgical instrument 35 respectively, and show the first and second sliders 60, 70 translated or moved distally from the first position of FIGS. 3–4 to the second position by the trigger 85. The distal movement of first and second sliders 60, 70 has extended the end effector 95 from the distal end of the shaft 92. The trigger 85 is in a first partially closed position and is poised to release the first slider 60 from the drive arm 90 of the trigger assembly.

In FIG. 5, as trigger 85 rotates counter-clockwise towards the grip 43, the drive arm 90 rotates into operative engagement with the guide rib 68 and moves the first slider 60 distally. As first slider 60 moves distally, the forked stops 78 of the second slider 70 are contacted, pushing the second slider 70 distally. The distally moving first and second sliders 60, 70 compress the first and second return springs 115, 116 as shown. The lockout arm 88 of the trigger assembly is moving upwardly, and is rotating the lockout wheel 100.

In FIG. 6, as the first and second sliders 60, 70 move distally, they deflect the latch post 57 of the latch 55 downwardly to slide along the first ramp 69a of the first slider 60 and a second ramp 80 of the second slider 70. Latch post 57 of the latch 55 passes the second ramp 80 and deflects upwardly to lock against a third ramp 81 of the second slider 70 and against a bottom surface 62a of the first sequencing member 62. With the latch 55 in this position, the second slider 70 is locked in the distal position and cannot move proximally.

Figure 7:
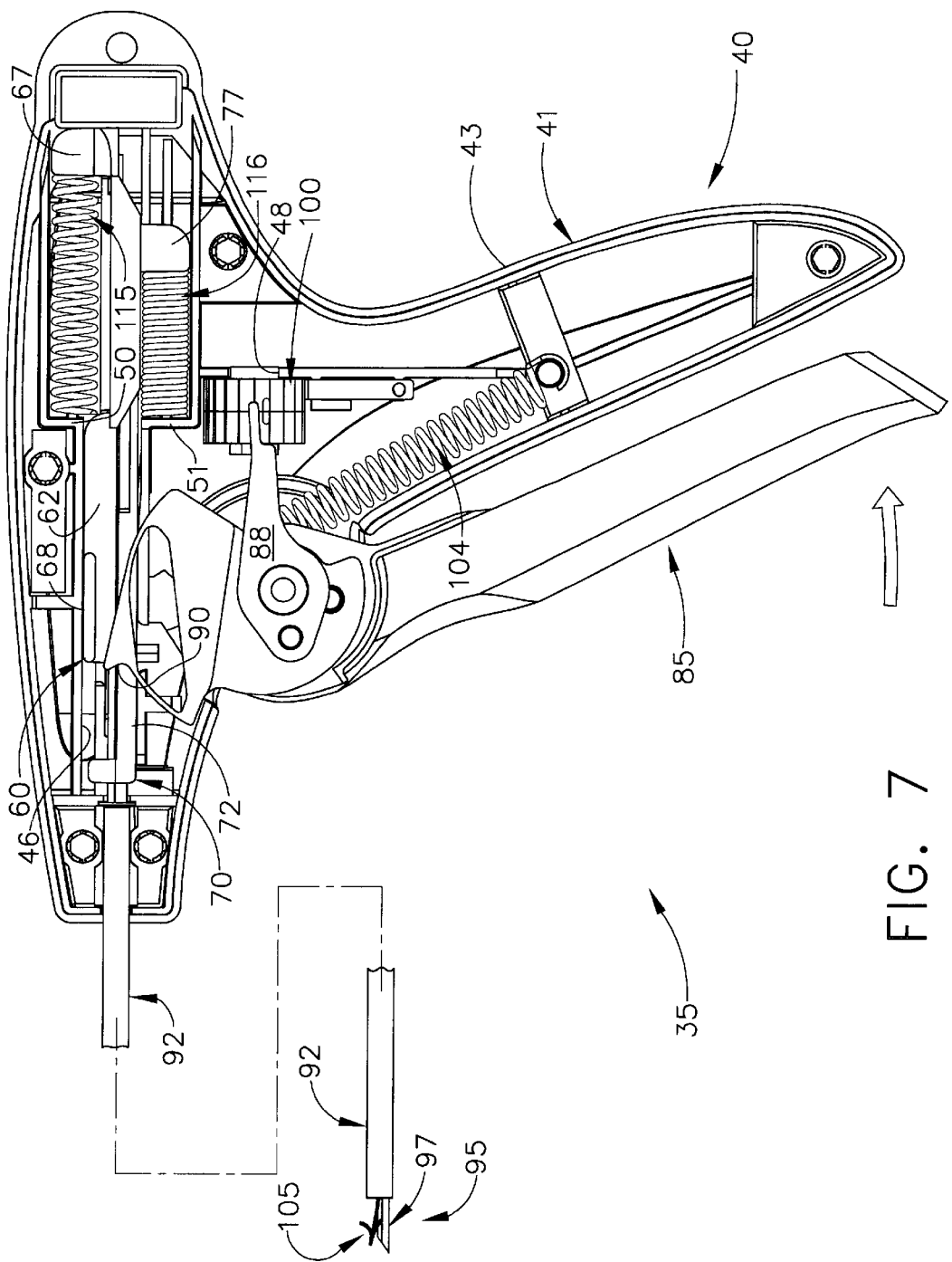
FIG. 7 is a side view of the first side of the surgical instrument of FIG. 5 wherein the trigger is moved to a fully closed position to retract a first portion of the end effector into the surgical instrument, and to expose a portion of a fastener at the end effector.
Figure 8:
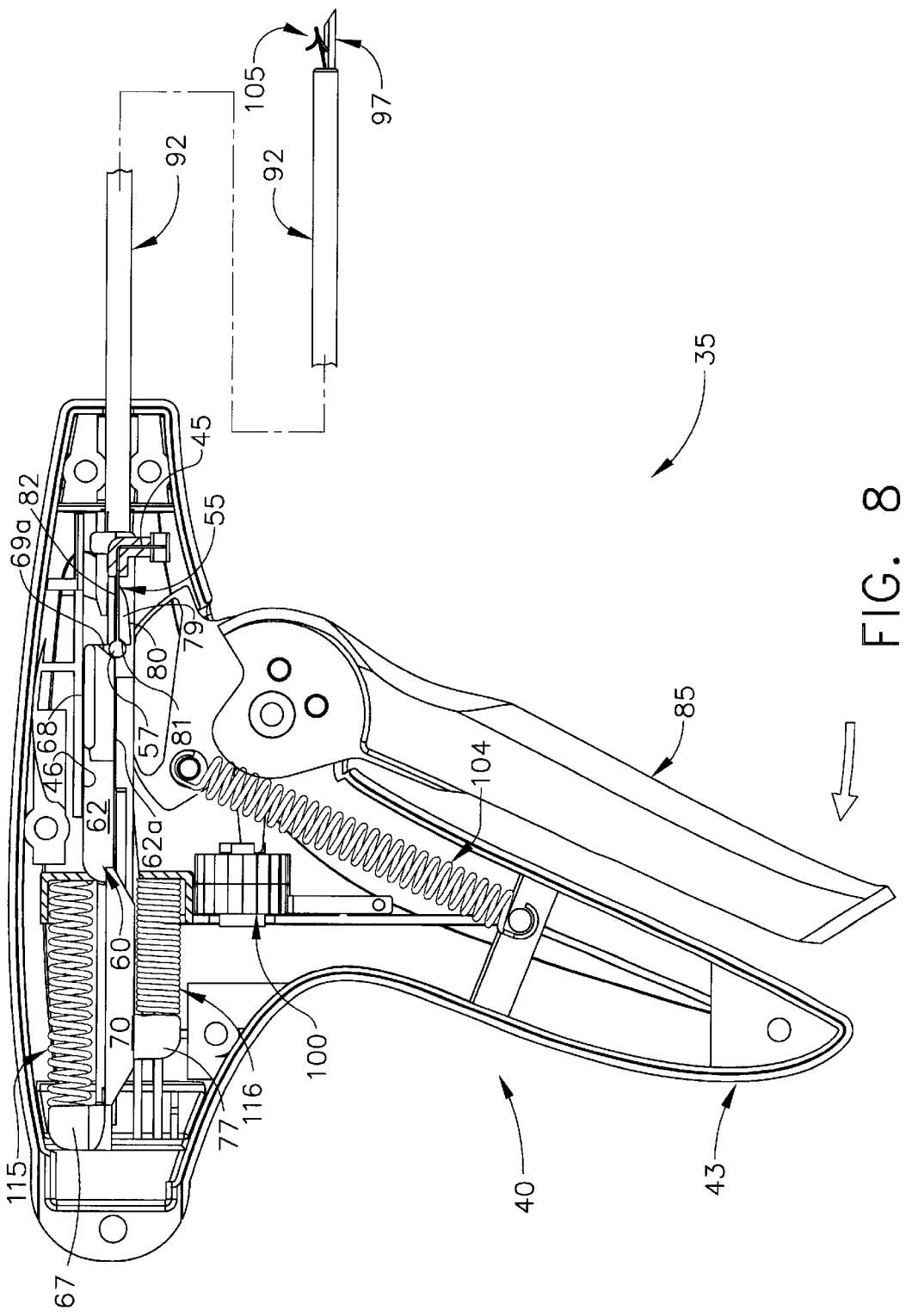
FIG. 8 is the view of the second side of the surgical instrument of FIG. 7, wherein the trigger is moved to a fully closed position to retract an upper portion of the end effector into the surgical instrument, and to expose a portion of a fastener at the end effector.

FIGS. 7 and 8 show the left and right side views of the assembled surgical instrument 35 respectively, after the first slider 60 has reciprocated or returned back to the first proximal position of FIGS. 3 and 4 to partially release a fastener 105 from the end effector 95.

As shown in FIG. 7, after the guide rib 68 is released from the drive arm 90, the first slider 60 reciprocates distally to the first proximal position from the second distal position shown in FIGS. 5 and 6. Slider 60 was returned to the proximal position by first return spring 115. The proximal movement of the first slider 60 retracted the first stab plate 96 proximally into the shaft 92 and released a distal end of the fastener 105 as shown. The lockout arm 88 moved upwardly from and disengaged with the lockout wheel 100.

In FIG. 8, as first sequencing member 62 moves proximally, the bottom surface 62a of the first sequencing member 62 moves distally away from the latch post 57 enabling the latch 55 to deflect upwardly to the un-deflected position shown in FIG. 3. This movement unlocks the second sequencing member 72. With the second sequencing member 72 unlocked, the compressed second return spring 116 will reciprocate the second slider 70 back to the original proximal position of FIG. 3. As the second slider 70 reciprocates back to the first proximal position, latch post 57 is deflected upwardly by the third ramp 81 of the cam plate 79 to travels over a top surface 82 of the distally moving cam plate 79 and returns to the position of FIG. 3. At this point, if an instrument lockout is not actuated, the trigger 85 is released to bring the elements of the instrument back to the positions shown in FIG. 3.

The Fastener

FIGS. 9–13 are expanded views showing the novel surgical element, anchor, or fastener 105 of the present invention. A plurality of fasteners 105 of the present invention are contained serially within the surgical instrument 35 (FIG. 2B) and are used to fasten or suture a prosthetic such as a surgical mesh pad onto tissue. The fastener 105 of the present invention is elastic and is shown in its original unconstrained state in FIGS. 9 and 10. When fastener 105 is distorted or constrained, it will return to its original shape when released. Fastener 105 can be formed or stamped from a sheet or foil of a pseudoelastic or superelastic nickel titanium alloy to take advantage of pseudoelastic or superelastic properties thereof, or an elastic or spring grade of steel, stainless steel, copper, or other titanium alloys.

Most preferably, fastener 105 is made from an alloy comprising from about 50.5% (as used herein these percentages refer to atomic percentages) Ni to about 60% Ni, and most preferably about 55% Ni, with the remainder of the alloy Ti. Preferably, the fastener is such that it is superelastic at body temperature, and preferably has an Af in the range from about 24° C. to about 37° C. The superelastic design of the fastener 105 makes it crush recoverable which makes it possible to store a large fastener 105 within a small diameter shaft 92.

As mentioned above, it is preferred that the fastener 105 of the present invention be made from a superelastic alloy and most preferably made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) is below human body temperature and preferably is about 24° C. to about 37° C. so that austenite is the only stable phase at body temperature.

Figures 9, 10:
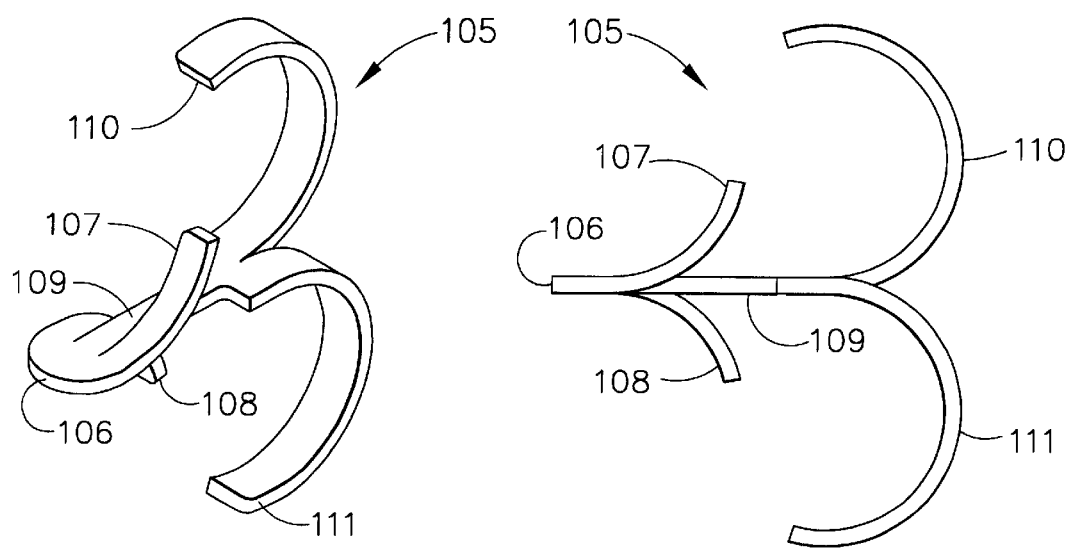
FIG. 9 is an isometric view of a fastener of the preferred invention wherein the fastener of the preferred invention has a pair of distal barbs and a pair of longer proximal arms, the fastener of the preferred invention is shown in an unconstrained state.
FIG. 10 is a side-view of FIG. 9 wherein the fastener of the preferred invention is shown in an unconstrained state.

The unconstrained fastener 105 of FIGS. 9 and 10 has a generally planar continuous body member 109 having a first (distal) end and a second (proximal) end. At least one barb extends from the distal end, and at least two barbs extend from the proximal end. The continuous body member 109 has a distal tip 106 which is rounded or blunt, as the fastener 105 does not need to penetrate tissue. Alternately, the distal tip 106 of the fastener 105 can be made sharp or pointed if desired. A first and a second barb 107,108 extend proximally and axially away from the distal tip 106 and away from the body member 109. The first and second barbs 107, 108 can be curved. The distal end of the body member 109 has a pair of barbs or a first and a second leg 110, 111 that extend distally from the body member 109 and away from each other in different directions. First and second legs 110, 111 of the present invention engage the inner surfaces of the first and second members 60,70, can also be curved outwardly from the body member 109, and can form the everted configuration f FIGS. 9 and 10. The ends of the first and second barb 107, 108, and first and second leg 110, 111, can be blunt.

Figure 11:
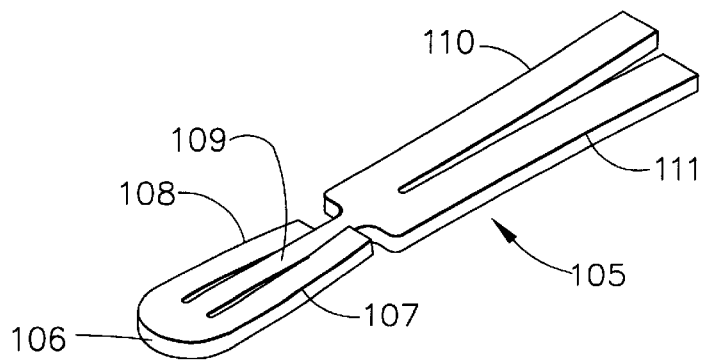
FIG. 11 is an isometric view of the fastener of FIG. 9 wherein the fastener of the preferred invention is shown in a constrained state as found within the surgical instrument of FIG. 1.
Figure 12:
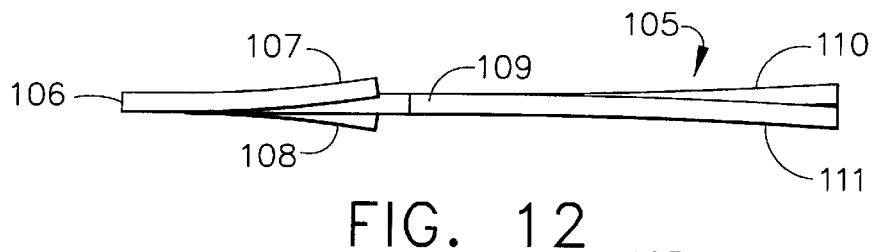
FIG. 12 is a side-view of FIG. 11 wherein the fastener of the preferred invention is shown in a constrained state.
Figure 13:
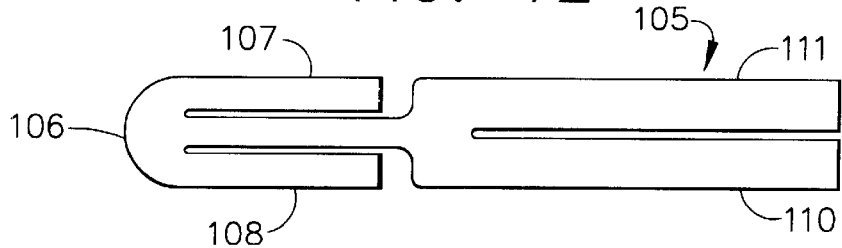
FIG. 13 is a bottom-view of FIG. 12 wherein the fastener of the preferred invention is shown in a constrained state.

FIGS. 11–13 shows an isometric view, a side view, and a bottom view of the fastener 105 of the present invention wherein the fastener 105 is shown in a constrained state that the fastener 105 assumes when stored within the surgical instrument 35 (FIG. 1). The fastener 105 will revert to the unconstrained shape of FIGS. 9 and 10 when released from the surgical instrument 35. Surgical fastener 105 can also be used as a marker when placed in tissue. That is, the material of the fastener 105 is such that it appears in diagnostic tests such as MRI scans, CAT scans, X-rays, or ultrasound, and the surgeon can readily identify the location of the fastener relative to other body features.

The Drive Mechanism

The drive mechanism is novel as it uses the fasteners 105 themselves as a part of the drive mechanism. As shown in FIG. 14, the drive mechanism 59 has three distinct elements: the first member or slider 60, the second member or slider 70, and the plurality of fasteners 105 stored in a serial fashion therebetween. Fasteners 105 are held between the sawteeth 120 with the barbs 107, 108 deflecting outwardly to center the fasteners 105 between the sawteeth 120. First and second legs 110, 111 of the fasteners 105 are biased outwardly, contacting the surfaces of the sawteeth 120 at an angle as shown. The corners of the legs 110, 111 where they contact the first and second sliders 60, 70 will dig into and attempt to expand outwardly against the sawteeth if the fasteners 120 are moved proximally relative to the first or second slider. Also the distal ends of the legs can form positive contact with the steps 121 of the sawteeth 120. Distal movements of the fasteners within the first and second sliders 60, 70 slide the corners of the legs 110, 111 along the inclines 122. Additionally, the corners of the barbs 107, 108 contact the inclines 122 and act in a similar manner as the legs 110, 111 when they engage the first and second sliders 60, 70. The distal ends of the first and second legs 110, 111 are shown positioned within the pockets at the junction of the step 121 and the incline 122, and are operatively engaged with the steps 121 and slidingly engaged with the inclines 122. It is the positive contact or engagement of the fasteners 105 with the steps 121 and sliding contact or engagement with the inclines 122 that drives or feeds the plurality of fasteners 105 between the reciprocating first and second sliders 60,70 and places the fastener 105 into tissue. Thus, both the barbs 107, 108 and the legs 110, 111 can propel the fasteners.

To someone skilled in the art, it can be seen that given the elements of the drive mechanism 59 described above, distal movement of both of the first and second sliders 60, 70 results in operative engagement of the fasteners 105 with the steps 121 of both sliders 60, 70. This operative engagement with the distally moving sliders 60, 60 will result in distal movement of the fasteners 105. If one of the sliders such as first slider 60 is moved distally while the other remains stationary, the fasteners 105 operably couple with and move with the moving slider 60, while slidingly engaging with the stationary slider 70. And, if one of the sliders such as first slider 60 moves proximally while the other remains stationary, the fasteners 105 operatively engage with the stationary slider 70 and remain stationary and slidably engaged with the moving slider 60.

With the above combinations of motions and reactions, there are three different sequences of motion possible with the sliders 60, 70 that will drive the fasteners 105 distally through the surgical instrument 35 (FIG. 3). One of these sequences of motion was selected for use with the surgical instrument 35 of the present invention, as it is best suited to place a fastener 105 into tissue. This driving sequence using the drive mechanism 59 of the present invention is shown in a step by step manner beginning with the start position shown in FIG. 14, and finishing in FIGS. 18–22. The other two driving sequences will be described later.

The actuator mechanism of the present invention has at least three sequential positions. First, the actuator mechanism moves the first and second sliders 60, 70 distally (FIGS. 18, 19) from a first proximal position (FIG. 14) to a second distal position (FIG. 19). This movement positively engages the fasteners 105 with the first and second sliders 60, 70 and moves the fasteners 105 distally from the first position to the second position. Moving both the first and second sliders 60, 70 (FIG. 14) from a first proximal position to a second distal position moves the entire plurality of fasteners 105 distally within the surgical instrument 35. That is, each fastener 105 (with the exception of the distalmost fastener 105) now occupies the position of the preceding fastener 105.

Figure 20:
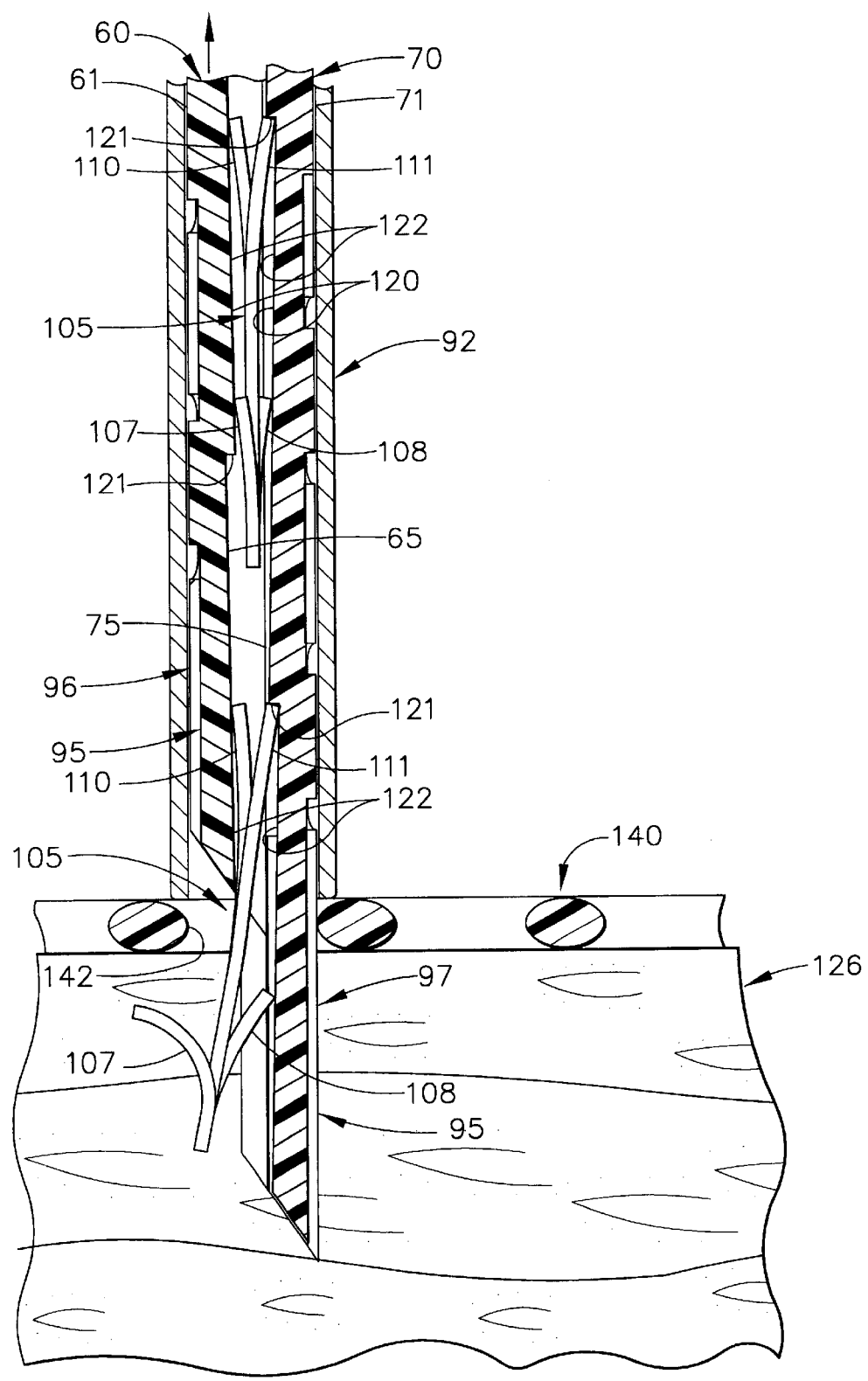
FIG. 20 is a cross-sectional side view of the inguinal floor and instrument of FIG. 19 wherein a first portion of the end effector is partially retracted into the shaft to deploy a first barb of the fastener of the preferred invention contained therein and to engage the first barb with the inguinal floor.
Figure 21:
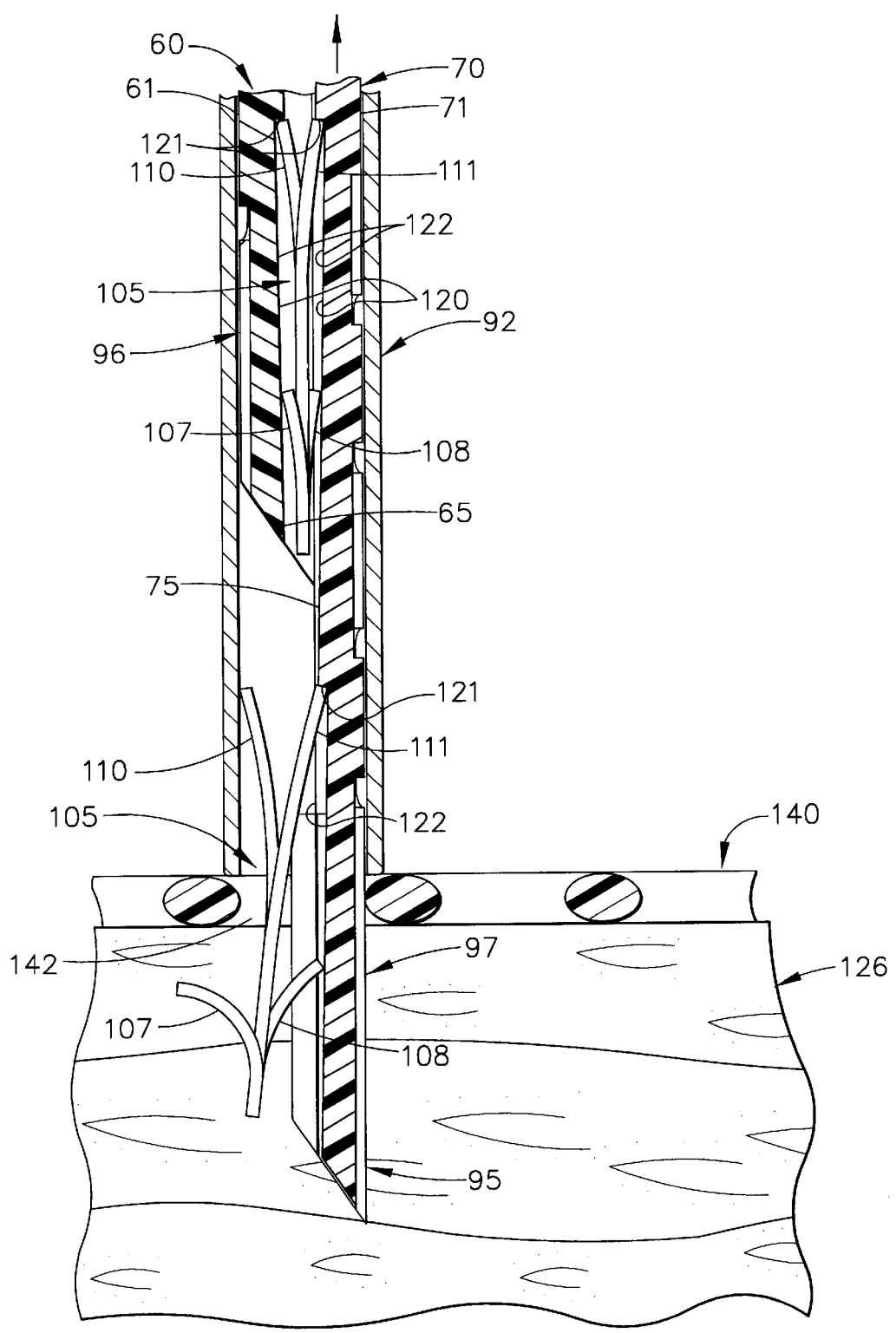
FIG. 21 is the cross-sectional side view of FIG. 20 wherein the first portion of the end effector of the present invention is fully retracted into the shaft, the full retraction releasing the arms of the fastener of the preferred invention into the portion of the shaft previously occupied by the first portion of the end effector.

Next, as shown in FIGS. 20, 21, the actuator mechanism moves or reciprocates the first slider 60 proximally from the second distal position back to the first proximal position to opposedly align the sawteeth 120 of the first and second sliders 60, 70. As shown, the fasteners 105 are operatively engaged with the stationary second slider 70 and remain stationary (longitudinally) within the shaft 92.

Figure 22:
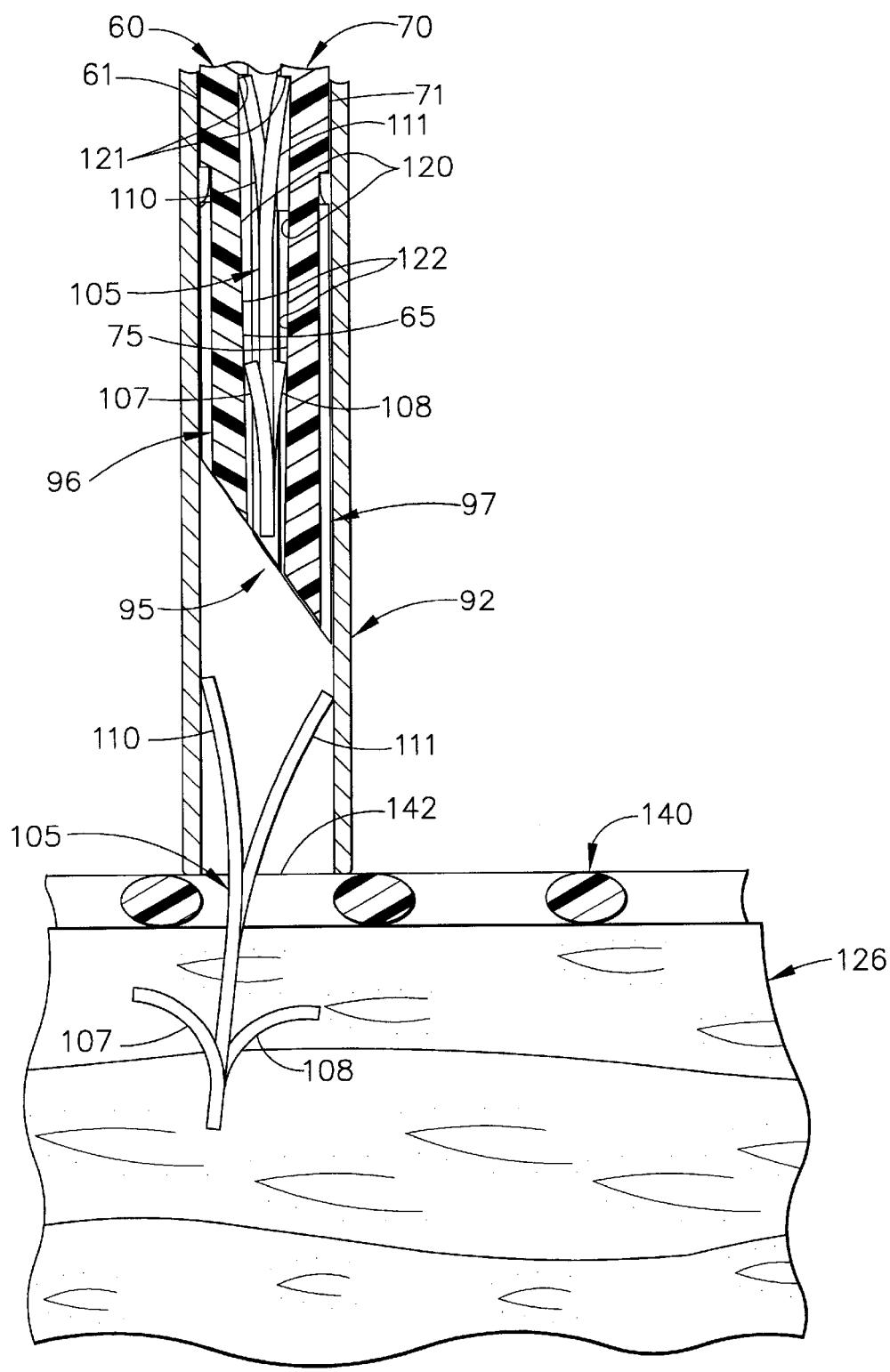
FIG. 22 is the cross-sectional side view of FIG. 21 wherein a second portion of the end effector of the present invention is fully retracted into the shaft, the full retraction engaging a second barb of the fastener of the preferred invention with the inguinal floor and both arms with the shaft.

Finally, as shown in FIG. 22 the actuator mechanism moves or reciprocates the second slider 70 proximally from the second distal position back to the first proximal position, and to realign the sawteeth 120 within the first and second sliders 60, 70. The fasteners 105 in operative contact with the stationary first slider 60 remain stationary and in sliding contact with the distally moving second slider 70. As shown in FIG. 22, the first and second sliders 60, 70 have placed the distalmost fastener 105 within tissue and have moved distally back to the first position. A new fastener 105 is shown within first and second sliders 60, 70, ready for placement within tissue.

As described above, there are two additional embodiments of the present invention wherein different sequences of motion are possible with the first and second sliders 60, 70. These alternate sequences of motion will also drive the fasteners 105 distally through the surgical instrument 35 (FIG. 3).

In the next or second embodiment, the sequence of motion is to fix one of the first or sliders such as first slider 60 and to reciprocate the remaining slider 70 distally from the first position to the second position and back to the first position. In the third embodiment, the sequence of motion is altered wherein the first and second sliders 60, 70 are reciprocated in opposite directions at the same time.

The Anatomy

Figure 16:
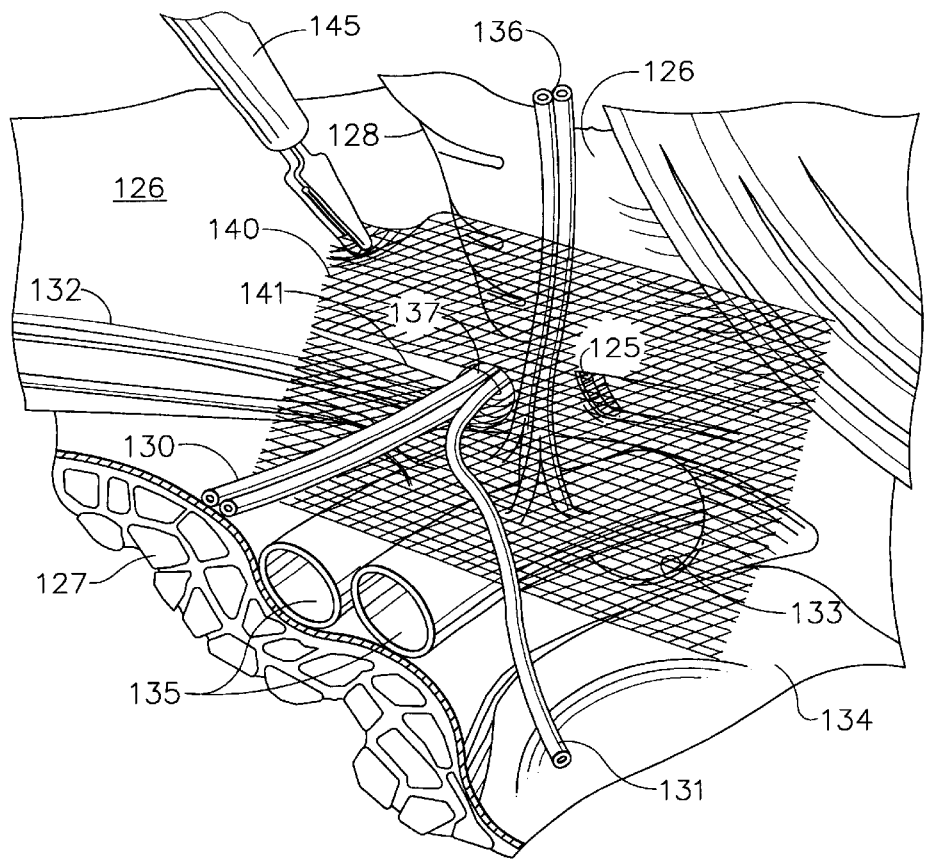
FIG. 16 is a fragmentary perspective view of a surgical grasper instrument placing a mesh patch over a defect or hernia in the inguinal floor of the lower abdomen, particularly the left inguinal anatomy.

Referring now to FIG. 16, one typical application of the surgical instrument of the present invention is a repair of a defect, such as an inguinal hernia 125, located in inguinal tissue such as the inguinal floor 126. The anatomical structures of the left inguinal anatomy of a human patient are illustrated in order to point out the usefulness of the present invention.

Generally, the inguinal hernia 125 is accessible through iliacus muscle 127. As can be well appreciated, a network of vessels and nerves exist in the area of a typical inguinal hernia 125, which requires a surgeon to conduct a hernia repair with great skill and caution. For instance, in the transverse abdominis aponeurosis 128, an internal ring 129 permits gastric vessels 130 and Vas deferens 131 to extend therethrough over an edge of inguinal ligament 132. Femoral canal 133 is located near Cooper's ligament 134 and contains external iliac vessels 135 and inferior epigastric vessels 136.

In many cases, the edge of the inguinal ligament 132 and Cooper's ligament 134 serve as anatomical landmarks and support structures for supporting surgical fasteners such as those mentioned previously. The area containing the external iliac vessels 135 and the Vas deferens 131 is commonly known as "the Triangle of Doom" to surgeons. Accordingly, the surgeon should avoid injuring any of these vessels described above and care must be taken when performing dissection, suturing or fastening within this area.

Figure 17:
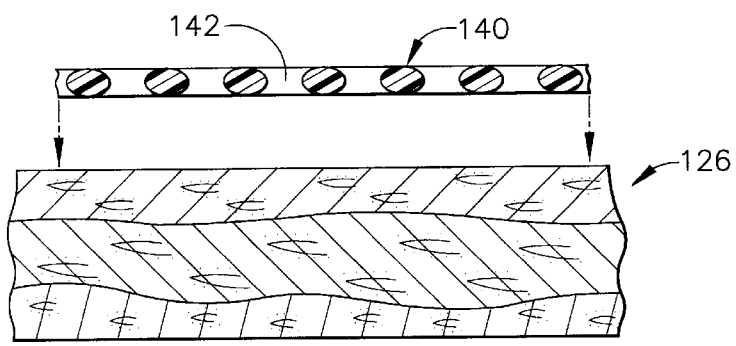
FIG. 17 is a cross-sectional side view of the inguinal floor of the lower abdomen of FIG. 16 illustrating the placement of the mesh patch above the tissue in preparation for repair of the defect, according to the present invention.

In FIGS. 16 and 17, a prosthetic or a mesh patch 140 is placed over the inguinal hernia 125 with a surgical grasping instrument 145 as the first step in the repair of the inguinal hernia 125. The mesh patch 140 may consist of any desired configuration, structure or material. However, the mesh patch 140 is preferably made of PROLENE™ (a known polymer made up of fibers) and preferably configured as mesh. It is within the training and comfort zone for surgeons to use the PROLENE™ mesh patch 140 since the mesh patch 140 is easily sized, such as providing a side slot 141, for accommodating the gastric vessels 130 and the Vas deferens 131.

As illustrated, the mesh patch 140 is placeable over the inguinal hernia 125 for providing a sufficient barrier to internal viscera (not shown) of the abdomen which would otherwise have a tendency to protrude through the inguinal hernia 125 and cause the patient a great deal of pain and discomfort. FIG. 11 shows a side view of the mesh patch 140 being placed onto the inguinal floor 126. The mesh patch 140 is now attachable to the inguinal floor 126.

The Method

FIGS. 18–23 are also used to illustrate the method of use of the surgical instrument 35. These cross-sectional side views of the distal end of the shaft 92 show the steps involved in using the surgical instrument 35 as it pierces tissue and delivers or places a novel surgical element or fastener 105 of the present invention into the inguinal floor 126 to attach the mesh patch 140 thereto.

Figure 18:
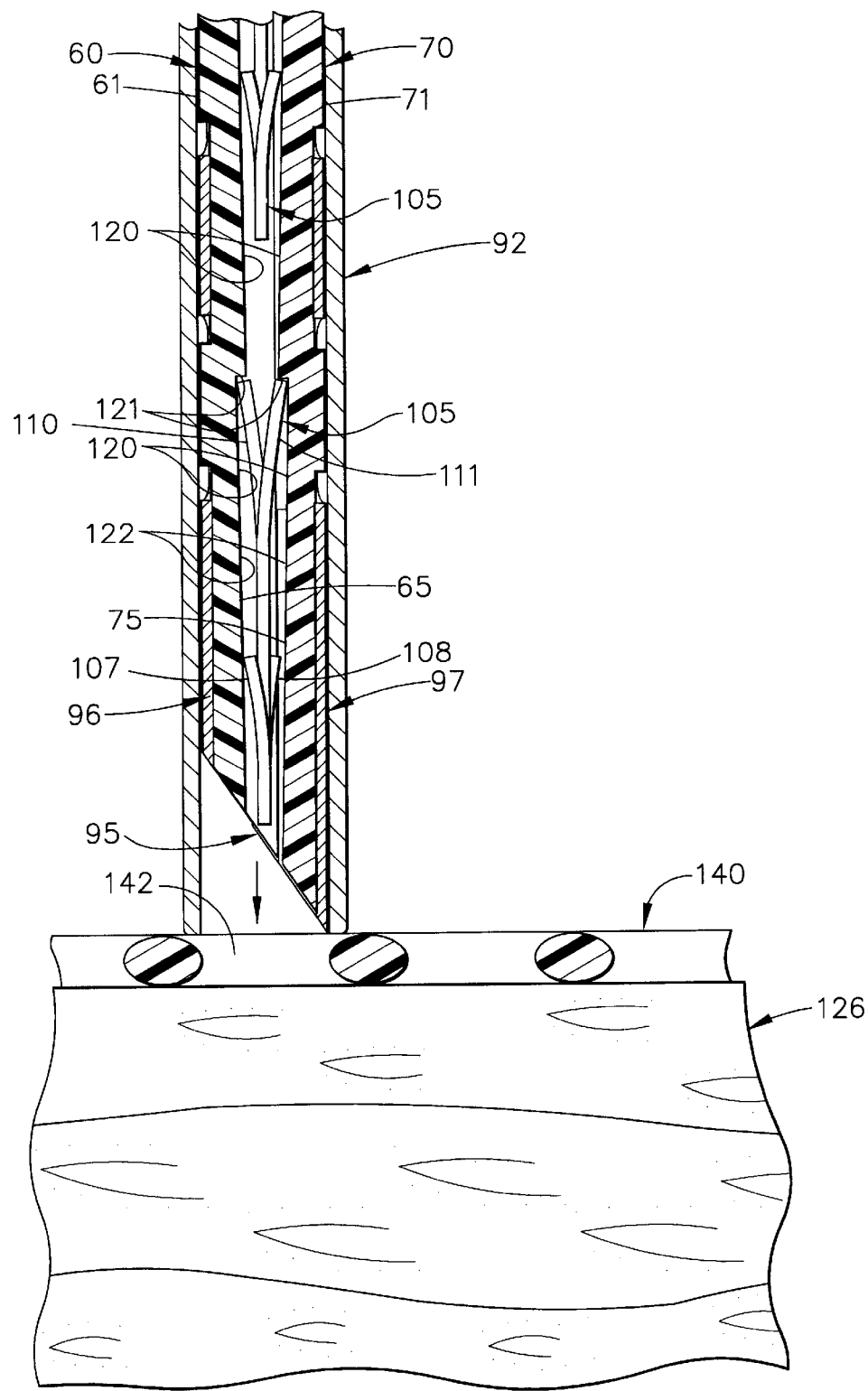
FIG. 18 is a cross-sectional side view of the inguinal floor of the lower abdomen wherein the distal end of the shaft of FIG. 14 is pushing the mesh patch downward onto the inguinal floor, and the end effector is moving downwardly within the shaft with a fastener contained therein.
Figure 19:
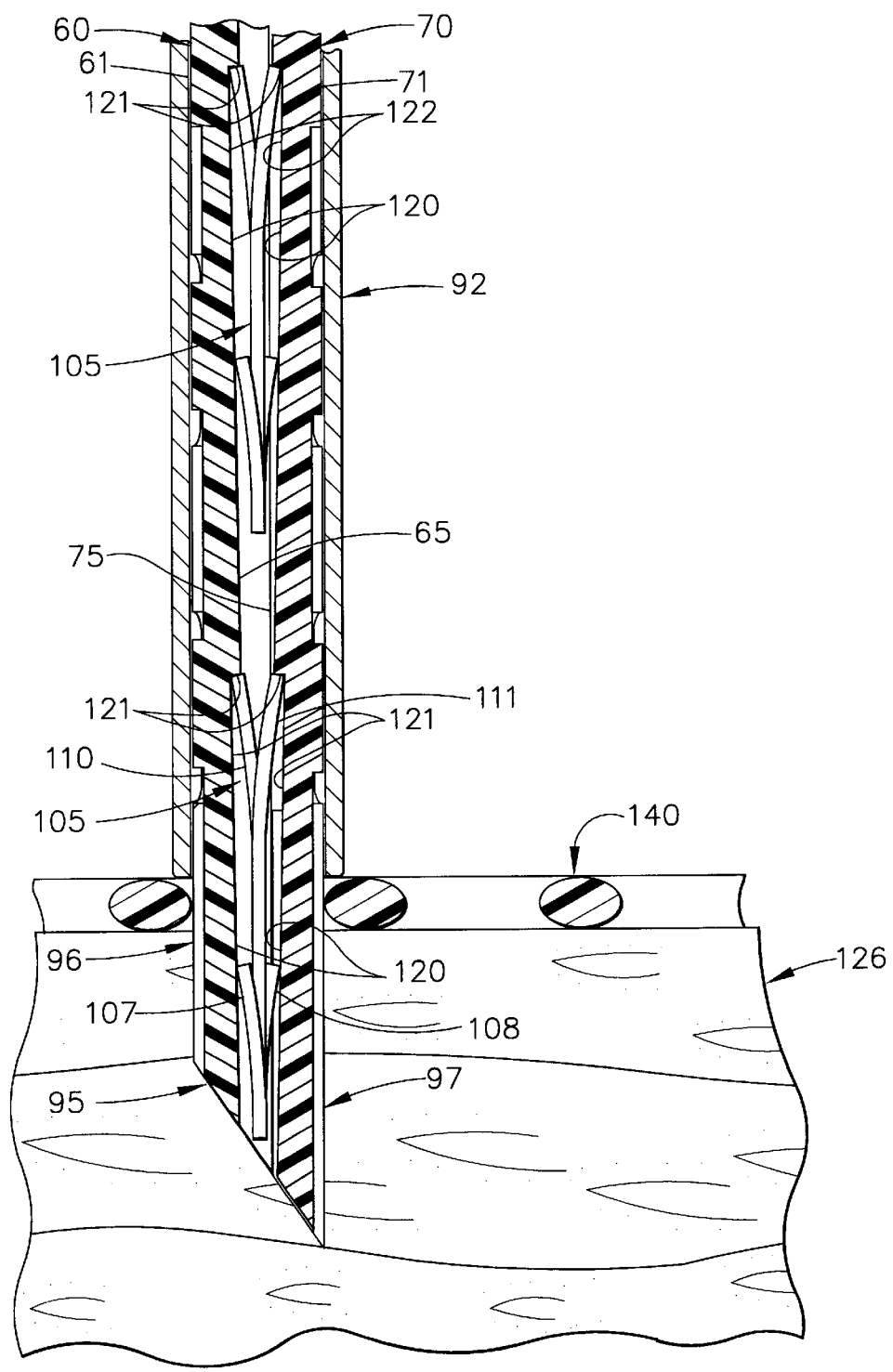
FIG. 19 is a cross-sectional side view of the inguinal floor and instrument of FIG. 18 wherein the end effector of the present invention is extended from the shaft and into the inguinal floor, the end effector containing a fastener of the preferred invention therein.

FIG. 18 is a cross-sectional side view of the inguinal floor 126 of the lower abdomen wherein the surgeon has placed the distal end of the shaft 92 into the area near the patient's inguinal hernia 125. The surgeon has selected an attachment point or surgical site and is using the distal end of the surgical instrument 35 to push the mesh patch 140 downward onto the inguinal floor 126. The distal end of the shaft 92 is deliberately positioned over an opening 142 within the mesh patch 140 for the placement of a fastener 105 therethrough. The position of the end effector 95 within the cross-sectioned shaft 92 indicates that the trigger 85 has been partially activated by the surgeon. The partial movement or activation of the trigger 85 is translating or moving the first and second sliders 60, 70 distally (downwardly in FIG. 14) from the initial position shown in FIG. 14.

As illustrated in FIG. 19, the surgeon has continued to actuate or move the trigger 85, has moved the trigger 85 to the first position (FIGS. 2, 5, and 6), and has fully extended or translated the first and second sliders 60, 70 of the end effector 95 from the shaft 92. The extended end effector 95 has penetrated through the opening 142 within the mesh patch 140 and into the inguinal floor 126. Although shielded from tissue contact by the end effector 95, the first and second barbs 107, 108 of the distalmost fastener 105 are placed within tissue of the inguinal floor 126.

Continued actuation of the trigger 85 by the surgeon moves the trigger 85 from the from the first partially closed position shown in FIGS. 5 and 6 to the second fully closed position shown in FIGS. 7 and 8. In this position, the indexing mechanism of the surgical instrument 35 of the preferred invention is actuated and an automatic sequence of actions occurs beginning with the reciprocation or movement of the first slider 60 proximally as indicated by the arrow in FIG. 20.

In FIG. 20, the first slider 60 has partially moved or retracted into the shaft 92. This action has released the first and second barbs 107, 108 of the distalmost fastener 105 from the constrained condition shown in FIG. 19 and fixably engaged the first barb 107 with the tissue of the inguinal floor 126. The barbs 107, 108 of the distal fastener 105, when released, snap open to the positions shown in FIG. 20, bending the distalmost fastener 105.

Once actuated, the first slider 60 continues to move distally into the surgical instrument 35 until it returns to the to the initial start position within the shaft 92 as shown in FIG. 21. When the first slider 60 is at this position, the second slider 70 is automatically released to move or reciprocate distally into the shaft 92 as indicated by the arrow.

As shown in FIG. 21, the first slider 60 is at to the initial start position of FIG. 10, fully releasing the distal fastener 105. The second barb 108 and second leg 111 bias the distal fastener 105 into the portion of the shaft 92 previously occupied by the first feed member 61 of the first slider 60. This bias further engages the first barb 107 of the distal fastener 105 with the inguinal floor 126.

In FIG. 22, the second slider 70 has automatically retracted distally into the shaft 92 to the first start position and has fully released the second barb 108 of the distal fastener 105 to engage with the tissue of the inguinal floor 126. The second leg 111 of the distal fastener 105 has also been released from the second slider 70 and both the first and the second legs 110, 111 have expanded outwardly within the shaft 92.

Figure 23:
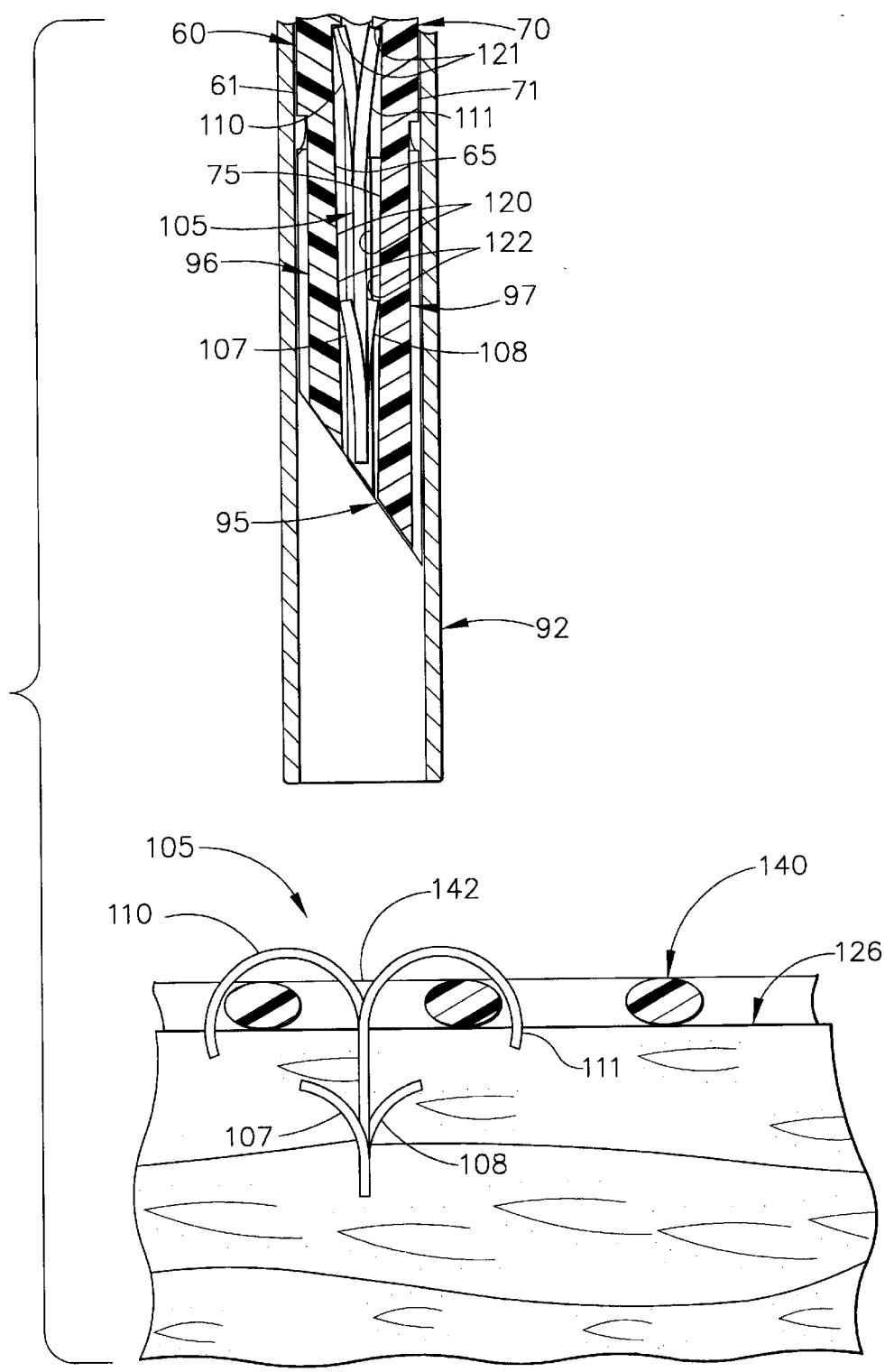
FIG. 23 is a cross sectional side view of FIG. 22 wherein the shaft of the surgical instrument of FIG. 22 has moved upwardly to release the arms of the fastener of the preferred invention, the released arms attaching the surgical mesh to the inguinal floor.

Finally, the surgeon releases the trigger 85 which returns to the initial open position of FIG. 1 and withdraws the distal end of the shaft 92 away from the mesh patch 140, and from the distal fastener 105 that is engaged or attached to the inguinal floor 126. As shown in FIG. 23, the first and second barbs 107, 108 of the fastener 105 of the present invention are firmly planted within the inguinal floor 126 and the first and second legs 110, 111, when released from the shaft 92, snap back to their original everted shape (FIGS. 9 and 10). The mesh patch 140 is fixedly held against the inguinal floor 126 by the first and second legs 110, 111 of the fastener 105. The surgical instrument is now ready to attach the mesh patch 140 at another site. To accomplish this, the surgeon merely repositions the distal end of the shaft 92 at another surgical site and actuates the trigger 85 to place or attach another fastener 105 into the inguinal floor 126. This process is continued until the mesh patch 140 is satisfactorily attached to the inguinal floor 126.

The Lockout Mechanism

The surgical instrument 35 of the present invention (FIG. 1) contains a plurality of fasteners 105. As the surgeon repeatedly fires the instrument during the attachment of the prosthetic, the number of fasteners 105 stored therein steadily decreases. When the final fastener 105 is placed into tissue, the surgeon has no way of knowing when the instrument is emptied of fasteners 105 and can attempt to fire the empty surgical instrument 35 on tissue. A lockout mechanism of the preferred invention is provided within the surgical instrument 35 to lock the trigger 85 when the surgical instrument 35 is empty.

As described previously, the trigger 85 has a lockout arm 88 fixably attached to and extending therefrom. Actuation of the trigger 85 moves the lockout arm 88 from the initial position of FIG. 3 to a first partially closed position within the handle 40, and into contact with the lockout wheel 100 rotatably mounted within the wheel receptacle 48 as shown in FIG. 24.

Figure 24:
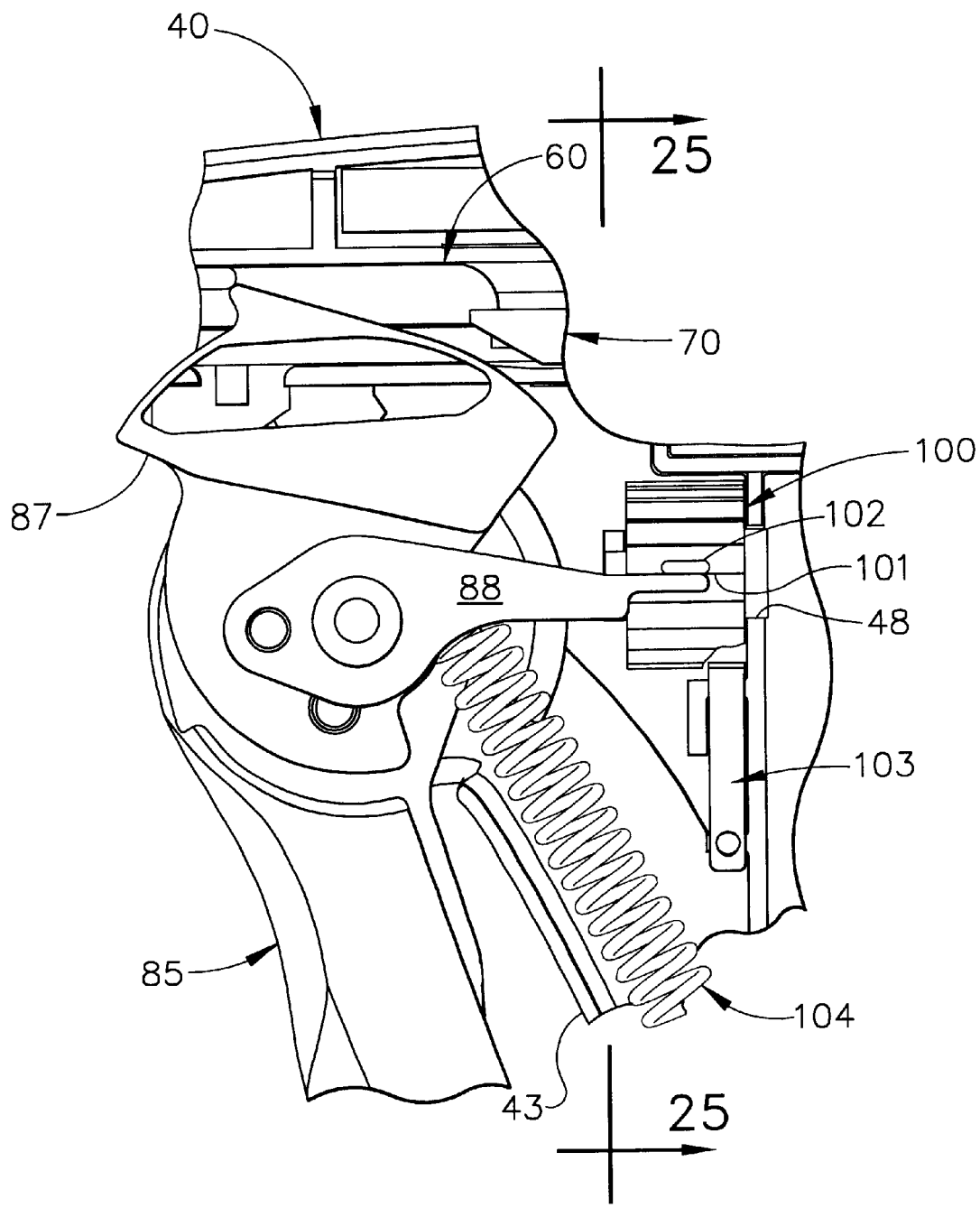
FIG. 24 is a is a fragmentary side-view of a trigger lockout mechanism of the present invention of FIG. 1 with a lockout arm fixably attached to the pivotable trigger, and operably coupled with a lockout wheel.

In FIG. 24, the trigger 85 has rotated lockout arm 88 counter-clockwise to engage with a tooth 101 of the lockout wheel 100. A lockout tab 102 is located just above the lockout arm 88 and extends outwardly from the lockout wheel 100. A lockout detent 103 is attached to and extends outwardly from the right handle half 41 towards the viewer to operably engage with the lockout wheel 100. A small cutout is provided within the lower portion of the lockout wheel 100 to show the outwardly extending end of the lockout detent 103.

FIG. 25 is a distal view taken across cross-section 25—25 in FIG. 24, and shows the necessary portions of the key elements so that the reader can understand the operation of the lockout mechanism. The lockout mechanism of the present invention consists of the lockout wheel 100, the lockout detent 103 and the lockout arm 88 extending from the trigger 85. Lockout wheel 100 is shown perpendicular to the axis of rotation and has lockout detent 103 operably engaged with a lockout tooth 101 to prevent clockwise rotation of the lockout wheel 100. The lockout arm is cross-sectioned by the cutting plane 25—25 and two cross-sections are taken across the lockout arm 88. A first section 88a is taken across the distal end of the lockout arm 88 when the lockout arm is in the initial position, and a second section 88b is taken across the lockout arm 88 to show the actual position of the lockout arm 88. An arrow is provided to identify the direction of motion of the second section 88b of the lockout arm 88.

The lockout wheel 100 of the present invention has the same number of teeth 101 around its circumference as the surgical instrument 35 has fasteners 105. When the trigger 85 is fully actuated to place a fastener 105 into tissue, the lockout arm 88 is brought into contact with the lockout wheel 100 to rotate or index the lockout wheel 100 counterclockwise one tooth 101 as shown in FIG. 26. When the trigger 85 is released after the actuation, the lockout detent 103 prevents the lockout wheel 100 from rotating clockwise as the lockout arm 88 returns to the initial position 88a. Thus, one full actuation of the trigger 85 rotates the locking wheel 100 one tooth 101, and firing all of the fasteners 105 rotates the lockout wheel 100 one full revolution.

FIGS. 27–29 show how the lockout tab 102 operatively locks the lockout arm 88 (and the trigger 85) in the fully actuated or closed position as the last fastener 105 is fired. In FIG. 27, the lockout wheel has rotated nearly one full revolution from the first position of FIG. 25. This is indicated by the new position of the lockout tab 102. The second section 88b of the lockout arm 88 is shown moving upwardly, has just cleared the lockout tab 102, and is contacting the final lockout tooth 101. In FIG. 28, the second section 88b of the lockout arm 88 is shown in the fully actuated or closed position and the lockout tab 102 has rotated in under the second section 88b of the lockout arm 88. When the trigger 85 is released, the second section 88b of the lockout arm 88 moves downwardly to contact the lockout tab 102 and rotates the lockout wheel 100 clockwise to engage tooth 101 with the lockout detent 103 (FIG. 29). The engagement with the lockout detent 103 prevents the lockout wheel 100 from rotating clockwise and locks the second section 88b of the lockout arm 88. Thus, in FIG. 29, the second section 88b of the lockout arm 88 (and trigger 85) is locked in the first partially closed position by the lockout detent 103 which prevents the trigger 85 of the surgical instrument 35 from opening.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for delivering a plurality of individual surgical fasteners, said method comprising:
   a. providing a surgical fastener delivery device having a drive mechanism with distal and proximal ends, said drive mechanism comprising first and second opposing members, said members being moveable proximally and distally with respect to said delivery device, and individually with respect to each other, said device having the plurality of surgical fasteners located between said first and said second members;
   b. penetrating tissue by moving said drive mechanism distally;
   c. partially deploying a distal end of one of the surgical fasteners by moving said first member proximally; and
   d. fully deploying said distal end of the surgical fastener by moving said second member proximally.

2. The method of claim 1 further including the step of fully deploying the surgical fastener by deploying a proximal end of said surgical fastener.

3. The method of claim 2 further including the step of placing a prosthetic onto said tissue prior to the step of penetrating tissue, wherein said step of penetrating tissue further includes the step of penetrating said prosthetic.

4. The method of claim 1 further including the step of withdrawing the surgical instrument from the penetrated tissue as said surgical element is delivered.

5. The method of claim 1 further including delivering additional fasteners by repeating steps b–d at least once.

6. A method for repairing a hernia within a patient, said method comprising:
   a. providing a surgical fastener delivery device having a drive mechanism with distal and proximal ends, said drive mechanism comprising first and second opposing members, said members being moveable proximally and distally with respect to said delivery device, and individually with respect to each other, said device having a plurality of surgical fasteners located between said first and said second members;
   b. placing a prosthetic over the hernia and tissue adjacent thereto;
   c. penetrating said prosthetic and said adjacent tissue by moving said drive mechanism distally;
   d. fully deploying a distal end of one of said surgical fasteners into tissue by sequentially moving said first member proximally and then said second member proximally; and
   e. fully deploying a proximal end of said fastener by deploying a proximal end of said surgical fastener to attach said prosthetic to the adjacent tissue.

7. The method of claim 6 further including the step of holding said prosthetic in place against the adjacent tissue with said surgical fastener delivery device.

8. A method for delivering a plurality of individual surgical fasteners, said method comprising:
   a. providing a surgical fastener delivery device having a drive mechanism with distal and proximal ends, said drive mechanism comprising first and second opposing members, said members being moveable proximally and distally with respect to said delivery device, and individually with respect to each other, said device having a plurality of superelastic self-expanding surgical fasteners in a restrained shape located between said first and said second members;
   b. penetrating tissue by moving said drive mechanism distally;
   c. partially deploying a distal end of said fastener by allowing said fastener to partially resume a relaxed shape within tissue by moving said first member proximally; and
   d. fully deploying said distal end of said fastener allowing said distal end of said fastener to assume a relaxed shape within tissue by moving said second member proximally.

9. The method of claim 8 further including the step of fully deploying the surgical fastener by deploying a proximal end of said surgical fastener.

10. The method of claim 9 further including the step of placing a prosthetic onto said tissue prior to the step of penetrating tissue, wherein said step of penetrating tissue further includes the step of penetrating said prosthetic.

11. A method for repairing a hernia within a patient, said method comprising:
   a. providing a surgical fastener delivery device having a drive mechanism with distal and proximal ends, said drive mechanism comprising first and second opposing members, said members being moveable proximally and distally with respect to said delivery device, and individually with respect to each other, said device having a plurality of superelastic self-expanding surgical fasteners in a restrained shape located between said first and said second members;
   b. placing a prosthetic over the hernia and tissue adjacent thereto;

c. penetrating said prosthetic and said adjacent tissue by moving said drive mechanism distally;
d. fully deploying a distal end of one of said surgical fasteners into tissue by allowing said distal end of said fastener to resume a relaxed shape within tissue by sequentially moving said first member proximally and then said second member proximally;
e. fully deploying a proximal end of said fastener to attach said prosthetic to the adjacent tissue by allowing said proximal end of said fastener to fully resume a relaxed shape.

12. The method of claim 6 further including the step of holding said prosthetic in place against the adjacent tissue with said surgical fastener delivery device.

13. The method of claim 1 further including the step of withdrawing the surgical instrument from the penetrated tissue as said surgical element is delivered.

14. The method of claim 1 further including delivering additional fasteners by repeating steps b–d at least once.

* * * * *